United States Patent
Bawendi et al.

(10) Patent No.: US 8,101,234 B2
(45) Date of Patent: *Jan. 24, 2012

(54) HIGHLY LUMINESCENT COLOR-SELECTIVE NANOCRYSTALLINE MATERIALS

(75) Inventors: Moungi Bawendi, Boston, MA (US); Klavs F. Jensen, Lexington, MA (US); Bashir O. Dabbousi, Dhahran (SA); Javier Rodriguez-Viejo, Sant Cugat del Valles (ES); Frederic Victor Mikulec, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/725,438

(22) Filed: Mar. 16, 2010

(65) Prior Publication Data

US 2011/0017950 A1  Jan. 27, 2011

Related U.S. Application Data

(60) Continuation of application No. 12/509,869, filed on Jul. 27, 2009, which is a continuation of application No. 11/502,493, filed on Aug. 11, 2006, now Pat. No. 7,566,476, which is a division of application No. 10/960,947, filed on Oct. 12, 2004, now Pat. No. 7,125,605, which is a continuation of application No. 10/642,578, filed on Aug. 19, 2003, now Pat. No. 6,861,155, which is a continuation of application No. 09/625,861, filed on Jul. 26, 2000, now Pat. No. 6,607,829, which is a continuation-in-part of application No. 08/969,302, filed on Nov. 13, 1997, now Pat. No. 6,322,901.

(60) Provisional application No. 60/145,708, filed on Jul. 26, 1999.

(51) Int. Cl.
*B05D 7/00* (2006.01)
(52) U.S. Cl. ...................... 427/218; 427/212
(58) Field of Classification Search .................. 427/212, 427/218
See application file for complete search history.

(56) References Cited

U.S. PATENT DOCUMENTS

| | | | |
|---|---|---|---|
| 3,996,345 A | 12/1976 | Ullman et al. |
| 4,238,195 A | 12/1980 | Boguslaski et al. |
| 4,250,205 A | 2/1981 | Constant et al. |
| 4,594,264 A | 6/1986 | Jensen |
| 4,637,988 A | 1/1987 | Hinshaw et al. |
| 4,738,932 A | 4/1988 | Yabusaki |
| 4,777,128 A | 10/1988 | Lippa |

(Continued)

FOREIGN PATENT DOCUMENTS

CA 2029942 5/1991

(Continued)

OTHER PUBLICATIONS

Mastsumoto et al., "Preparation of Monodisperse CdS Nanocrystals by Size Selective Photocorrosion," J. Phys. Chem. 100, pp. 13781-13785, 1996.*

(Continued)

*Primary Examiner* — Michael Cleveland
*Assistant Examiner* — Robert Vetere
(74) *Attorney, Agent, or Firm* — Steptoe & Johnson LLP

(57) ABSTRACT

A nanocrystal capable of light emission includes a nanoparticle having photoluminescence having quantum yields of greater than 30%.

38 Claims, 4 Drawing Sheets

U.S. PATENT DOCUMENTS

| | | | |
|---|---|---|---|
| 4,798,701 A | 1/1989 | David | |
| 4,802,951 A | 2/1989 | Clark et al. | |
| 4,814,668 A | 3/1989 | Tohda et al. | |
| 5,084,128 A | 1/1992 | Baker | |
| 5,101,827 A | 4/1992 | Goldenberg | |
| 5,147,841 A | 9/1992 | Wilcoxon | |
| 5,200,668 A | 4/1993 | Ohashi | |
| 5,212,426 A | 5/1993 | Kane | |
| 5,260,957 A | 11/1993 | Hakimi et al. | |
| 5,262,357 A | 11/1993 | Alivisatos et al. | |
| 5,293,050 A | 3/1994 | Chapple-Sokol et al. | |
| 5,304,786 A | 4/1994 | Pavlidis et al. | |
| 5,308,804 A | 5/1994 | Lee | |
| 5,319,209 A | 6/1994 | Miyakawa et al. | |
| 5,354,707 A | 10/1994 | Chapple-Sokol et al. | |
| 5,395,791 A | 3/1995 | Cheng et al. | |
| 5,422,489 A | 6/1995 | Bhargava | |
| 5,427,767 A | 6/1995 | Kresse et al. | |
| 5,434,878 A | 7/1995 | Lawandy | |
| 5,442,254 A | 8/1995 | Jaskie | |
| 5,448,582 A | 9/1995 | Lawandy | |
| 5,455,489 A | 10/1995 | Bhargava | |
| 5,460,831 A | 10/1995 | Kossovsky et al. | |
| 5,474,591 A | 12/1995 | Wells et al. | |
| 5,492,080 A | 2/1996 | Ohkawa et al. | |
| 5,496,536 A | 3/1996 | Wolf | |
| 5,499,260 A | 3/1996 | Takahashi et al. | |
| 5,505,928 A | 4/1996 | Alivisatos et al. | |
| 5,515,393 A | 5/1996 | Okuyama et al. | |
| 5,525,377 A | 6/1996 | Gallagher et al. | |
| 5,537,000 A | 7/1996 | Alivisatos et al. | |
| 5,541,948 A | 7/1996 | Krupke et al. | |
| 5,565,324 A | 10/1996 | Still et al. | |
| 5,585,640 A | 12/1996 | Huston et al. | |
| 5,613,140 A | 3/1997 | Taira | |
| 5,625,456 A | 4/1997 | Lawandy | |
| 5,674,698 A | 10/1997 | Zarling et al. | |
| 5,677,545 A | 10/1997 | Shi et al. | |
| 5,711,803 A | 1/1998 | Pehnt et al. | |
| 5,721,099 A | 2/1998 | Still et al. | |
| 5,736,330 A | 4/1998 | Fulton | |
| 5,747,180 A | 5/1998 | Miller et al. | |
| 5,751,018 A | 5/1998 | Alivisatos et al. | |
| 5,770,299 A | 6/1998 | Dannenhauer et al. | |
| 5,786,139 A | 7/1998 | Burke et al. | |
| 5,789,162 A | 8/1998 | Dower et al. | |
| 5,846,517 A | 12/1998 | Unger | |
| 5,856,814 A | 1/1999 | Yagyu | |
| 5,882,779 A | 3/1999 | Lawandy | |
| 5,906,670 A | 5/1999 | Dobson et al. | |
| 5,910,554 A | 6/1999 | Kempe et al. | |
| 5,922,537 A | 7/1999 | Ewart et al. | |
| 5,932,309 A | 8/1999 | Smith et al. | |
| 5,939,021 A | 8/1999 | Hansen et al. | |
| 5,952,665 A | 9/1999 | Bhargava | |
| 5,985,173 A | 11/1999 | Gray et al. | |
| 5,985,353 A | 11/1999 | Lawton et al. | |
| 5,990,479 A | 11/1999 | Weiss et al. | |
| 6,005,707 A | 12/1999 | Berggren et al. | |
| 6,023,540 A | 2/2000 | Walt et al. | |
| 6,054,495 A | 4/2000 | Markowitz et al. | |
| 6,103,868 A | 8/2000 | Heath et al. | |
| 6,106,609 A | 8/2000 | Yang et al. | |
| 6,114,038 A | 9/2000 | Castro et al. | |
| 6,139,585 A | 10/2000 | Li | |
| 6,157,047 A | 12/2000 | Fujita et al. | |
| 6,159,445 A | 12/2000 | Klaveness et al. | |
| 6,159,742 A | 12/2000 | Lieber et al. | |
| 6,165,440 A | 12/2000 | Esenaliev | |
| 6,167,297 A | 12/2000 | Benaron | |
| 6,179,912 B1 | 1/2001 | Barbera-Guillem et al. | |
| 6,207,229 B1 | 3/2001 | Bawendi et al. | |
| 6,207,392 B1 | 3/2001 | Weiss et al. | |
| 6,224,739 B1 | 5/2001 | Reetz et al. | |
| 6,225,198 B1 | 5/2001 | Alivisatos et al. | |
| 6,251,303 B1 | 6/2001 | Bawendi et al. | |
| 6,252,254 B1 | 6/2001 | Soules et al. | |
| 6,262,129 B1 | 7/2001 | Murray et al. | |
| 6,274,323 B1 | 8/2001 | Bruchez et al. | |
| 6,294,401 B1 | 9/2001 | Jacobsen et al. | |
| 6,306,610 B1 | 10/2001 | Bawendi et al. | |
| 6,306,736 B1 | 10/2001 | Alivisatos et al. | |
| 6,309,701 B1 | 10/2001 | Barbera-Guillem | |
| 6,312,906 B1 | 11/2001 | Cass et al. | |
| 6,319,426 B1 | 11/2001 | Bawendi et al. | |
| 6,322,901 B1 | 11/2001 | Bawendi et al. | |
| 6,326,144 B1 | 12/2001 | Bawendi et al. | |
| 6,337,117 B1 | 1/2002 | Maenosono et al. | |
| 6,355,432 B1 | 3/2002 | Fodor et al. | |
| 6,361,944 B1 | 3/2002 | Mirkin et al. | |
| 6,379,635 B2 | 4/2002 | O'Brien et al. | |
| 6,410,255 B1 | 6/2002 | Pollok et al. | |
| 6,417,340 B1 | 7/2002 | Mirkin et al. | |
| 6,423,551 B1 | 7/2002 | Weiss et al. | |
| 6,426,513 B1 | 7/2002 | Bawendi et al. | |
| 6,444,143 B2 | 9/2002 | Bawendi et al. | |
| 6,444,192 B1 | 9/2002 | Mattrey | |
| 6,447,698 B1 | 9/2002 | Ihara et al. | |
| 6,500,622 B2 | 12/2002 | Bruchez, Jr. et al. | |
| 6,501,091 B1 | 12/2002 | Bawendi et al. | |
| 6,506,564 B1 | 1/2003 | Mirkin et al. | |
| 6,530,944 B2 | 3/2003 | West et al. | |
| 6,548,168 B1 | 4/2003 | Mulvaney et al. | |
| 6,548,171 B1 | 4/2003 | Barbera-Guillem et al. | |
| 6,576,291 B2 | 6/2003 | Bawendi et al. | |
| 6,582,921 B2 | 6/2003 | Mirken et al. | |
| 6,602,671 B1 | 8/2003 | Bawendi et al. | |
| 6,607,829 B1 | 8/2003 | Bawendi et al. | |
| 6,610,491 B2 | 8/2003 | Mirkin et al. | |
| 6,617,583 B1 | 9/2003 | Bawendi et al. | |
| 6,633,370 B2 | 10/2003 | Lawandy | |
| 6,636,755 B2 | 10/2003 | Toida | |
| 6,645,721 B2 | 11/2003 | Mirken et al. | |
| 6,673,548 B2 | 1/2004 | Mirkin et al. | |
| 6,677,122 B2 | 1/2004 | Mirkin et al. | |
| 6,682,895 B2 | 1/2004 | Mirkin et al. | |
| 6,696,299 B1 | 2/2004 | Empedocles et al. | |
| 6,699,723 B1 | 3/2004 | Weiss et al. | |
| 6,709,825 B2 | 3/2004 | Mirkin et al. | |
| 6,720,411 B2 | 4/2004 | Mirkin et al. | |
| 6,727,065 B2 | 4/2004 | Weiss et al. | |
| 6,730,269 B2 | 5/2004 | Mirkin et al. | |
| 6,750,016 B2 | 6/2004 | Mirkin et al. | |
| 6,759,199 B2 | 7/2004 | Mirkin et al. | |
| 6,767,702 B2 | 7/2004 | Mirkin et al. | |
| 6,773,884 B2 | 8/2004 | Mirkin et al. | |
| 6,774,361 B2 | 8/2004 | Bawendi et al. | |
| 6,777,186 B2 | 8/2004 | Mirkin et al. | |
| 6,797,412 B1 | 9/2004 | Jain et al. | |
| 6,803,719 B1 | 10/2004 | Miller et al. | |
| 6,804,549 B2 | 10/2004 | Hayashi | |
| 6,812,334 B1 | 11/2004 | Mirkin et al. | |
| 6,815,064 B2 | 11/2004 | Treadway et al. | |
| 6,818,753 B2 | 11/2004 | Mirkin et al. | |
| 6,819,692 B2 | 11/2004 | Klimov et al. | |
| 6,821,337 B2 | 11/2004 | Bawendi et al. | |
| 6,828,432 B2 | 12/2004 | Mirkin et al. | |
| 6,846,565 B2 | 1/2005 | Korgel et al. | |
| 6,855,551 B2 | 2/2005 | Bawendi et al. | |
| 6,858,158 B2 | 2/2005 | Chittibabu et al. | |
| 6,861,155 B2 | 3/2005 | Bawendi et al. | |
| 6,861,221 B2 | 3/2005 | Letsinger et al. | |
| 6,864,626 B1 | 3/2005 | Weiss et al. | |
| 6,872,249 B2 | 3/2005 | Peng et al. | |
| 6,878,814 B2 | 4/2005 | Mirkin et al. | |
| 6,890,777 B2 | 5/2005 | Bawendi et al. | |
| 6,902,895 B2 | 6/2005 | Mirkin et al. | |
| 6,903,207 B2 | 6/2005 | Mirkin et al. | |
| 6,914,265 B2 | 7/2005 | Bawendi et al. | |
| 6,921,496 B2 | 7/2005 | Anderson et al. | |
| 6,927,069 B2 | 8/2005 | Weiss et al. | |
| 6,962,786 B2 | 11/2005 | Mirkin et al. | |
| 6,969,761 B2 | 11/2005 | Mirkin et al. | |
| 6,984,491 B2 | 1/2006 | Mirkin et al. | |
| 6,986,989 B2 | 1/2006 | Mirkin et al. | |
| 7,049,148 B2 | 5/2006 | Bawendi et al. | |
| 7,060,243 B2 | 6/2006 | Bawendi et al. | |

| | | |
|---|---|---|
| 7,098,320 B1 | 8/2006 | Mirkin et al. |
| 7,101,718 B2 | 9/2006 | Weiss et al. |
| 7,125,605 B2 | 10/2006 | Bawendi et al. |
| 7,138,098 B2 | 11/2006 | Bawendi et al. |
| 7,160,613 B2 | 1/2007 | Bawendi et al. |
| 7,169,556 B2 | 1/2007 | Park et al. |
| 7,181,266 B2 | 2/2007 | Frangioni et al. |
| 7,189,417 B2 | 3/2007 | Chen et al. |
| 7,208,587 B2 | 4/2007 | Mirkin et al. |
| 7,235,361 B2 | 6/2007 | Bawendi et al. |
| 7,250,499 B2 | 7/2007 | Mirkin et al. |
| 7,259,252 B2 | 8/2007 | Mirkin et al. |
| 7,314,764 B2 | 1/2008 | Weiss et al. |
| 2001/0023078 A1 | 9/2001 | Bawendi et al. |
| 2001/0040232 A1 | 11/2001 | Bawendi et al. |
| 2002/0066401 A1 | 6/2002 | Peng et al. |
| 2002/0071952 A1 | 6/2002 | Bawendi et al. |
| 2002/0072234 A1 | 6/2002 | Weiss et al. |
| 2002/0146714 A1 | 10/2002 | Lieber et al. |
| 2003/0017264 A1 | 1/2003 | Treadway et al. |
| 2003/0042850 A1 | 3/2003 | Bertram et al. |
| 2003/0099968 A1 | 5/2003 | Weiss et al. |
| 2003/0100130 A1 | 5/2003 | Weiss et al. |
| 2003/0113709 A1 | 6/2003 | Alivisatos et al. |
| 2003/0209105 A1 | 11/2003 | Bawendi et al. |
| 2004/0033345 A1 | 2/2004 | Dubertret et al. |
| 2004/0036085 A1 | 2/2004 | Sato et al. |
| 2004/0265622 A1 | 12/2004 | Sadasivan et al. |
| 2005/0020922 A1 | 1/2005 | Frangioni et al. |
| 2005/0020923 A1 | 1/2005 | Frangioni et al. |
| 2005/0038498 A1 | 2/2005 | Dubrow et al. |
| 2005/0113697 A1 | 5/2005 | Ottoboni et al. |
| 2005/0118631 A1 | 6/2005 | Bawendi et al. |
| 2005/0175540 A1 | 8/2005 | Oraevsky et al. |
| 2005/0220714 A1 | 10/2005 | Kauzlarich et al. |

FOREIGN PATENT DOCUMENTS

| | | |
|---|---|---|
| EP | 1 271 154 A2 | 1/2003 |
| WO | WO 91/06894 | 5/1991 |
| WO | WO 93/10564 | 5/1993 |
| WO | WO 93/26019 | 12/1993 |
| WO | WO 94/07142 | 3/1994 |
| WO | WO 94/11103 A1 | 5/1994 |
| WO | WO 95/29473 | 11/1995 |
| WO | WO 96/10282 A1 | 4/1996 |
| WO | WO 97/10175 | 3/1997 |
| WO | WO 98/04740 | 2/1998 |
| WO | WO 98/19963 A1 | 5/1998 |
| WO | WO 98/33070 | 7/1998 |
| WO | WO 98/36376 | 8/1998 |
| WO | WO 98/46372 | 10/1998 |
| WO | WO 98/55844 A1 | 12/1998 |
| WO | WO 99/19515 A1 | 4/1999 |
| WO | WO 99/26299 | 5/1999 |
| WO | WO 99/50916 A1 | 10/1999 |
| WO | WO 00/17103 A3 | 3/2000 |
| WO | WO 00/17642 A2 | 3/2000 |
| WO | WO 00/17655 A1 | 3/2000 |
| WO | WO 00/17656 A1 | 3/2000 |
| WO | 0 990 903 | 4/2000 |
| WO | 00/27365 | 5/2000 |
| WO | WO 00/27365 A1 | 5/2000 |
| WO | WO 00/27436 A1 | 5/2000 |
| WO | WO 00/28088 A1 | 5/2000 |
| WO | WO 00/28089 A1 | 5/2000 |
| WO | WO 01/07689 A2 | 2/2001 |
| WO | WO 2005/004253 A1 | 1/2005 |
| WO | WO 2005/017951 A2 | 2/2005 |

OTHER PUBLICATIONS

Empedocles et al., "Photoluminescence Spectroscopy of Single CdSe Nanocrystalite Quantum Dots," Phys. Rev. Letts. 77, pp. 3873, 1996.*

Kuno et al., "The band edge luminescence of surface modified CdSe nanocrystallites," J. Chem. Phys. 106, pp. 9669-9682 (Jun. 15, 1997).*

Bowen Katari, et al. "X-ray Photoelectron Spectroscopy of CdSe Nanocrystals with Applications of Studies of the Nanocrystal Surface," J. Phys. Chem. 1994, 98: 4109-4117.

Chemseddine, et al., "Highly Monodisperse Quantum Sized CdS Particles by Size Selective Precipitation," Ber. Bunsenges. Phys. Chem. 1993, 97(4): 636-637.

Hines, et al., "Investigation Into the Synthesis of ZnS Capped CdSe Semiconductor Nanocrystals," American Physical Society, Annual March Meeting, Mar. 17-22, 1996, Abstract #D33.19, 1996.

Talapin, et al., "Highly Luminescent Monodisperse CdSe and CdSe/ZnS Nanocrystals Synthesized in a Hexadecylamine-Thoctylphosphine Oxide-Trioctylphosphine Mixture." Nano Letters, 2001, 1(4): 207-211.

Vossmeyer et al., "CdS Nanoclusters: Synthesis, Characterization, Size Dependent Oscillator Strength, Temperature Shift of the Excitonic Transition Energy, and Reversible Absorbance Shift," J. Phys. Chem., 1994, 98: 7665-7673.

Xie et al., "Synthesis and Characterization of Highly Luminescent CdSe-Core CdS/$Zn_{0.5}$S/ZnS Multishell Nanocrystals," JACS, 2005, 127: 7480-7488.

Peng et al., "Kinetics of II-VI and III-V Colloidal Semiconductor Nanocrystal Growth: 'Focusing' of Size Distributions," JACS, 1998, 120: 5343-5344.

Van Sark et al., "Photooxidation and Photobleaching of Single CdSe/ZnS Quantum Dots Probed by Room-Temperature Time-Resolved Spectroscopy." J. Phys. Chem., 2001, 105: 8281-8284.

Life Technologies Corporation, Molecular Probes, Inc. and The Regents of the University of California v. Ebioscience, In c. Civil Action No. 10-CV-2127-IEG (NLS)—Defendant Ebioscience, Inc.'s Preliminary Invalidity Contentions.

Akerman, et al., "Nanocrystal Targeting in vivo," Proc. Natl. Acad. Sci. USA 99:12617-12621, 2002.

Alivisatos, "Perspectives on the Physical Chemistry of Semiconductor Nanocrystals," J. Phys. Chem. 100:13226-13229, 1996.

Alivisatos, et al., "Electronic states of semiconductor clusters: Homogeneous and inhomogeneous broadening of the optical spectrum," J. Chem. Phys. 89:4001-4011, 1988.

Alivisatos, et al., "Electron-vibration coupling in semiconductor clusters studied by resonance Raman spectroscopy," J. Chem. Phys. 90:3463-3468, 1989.

Alivisatos, et al., "Resonance Raman scattering and optical absorption studies of CdSe microclusters at high pressure," J. Chem. Phys. 89:5979-5982, 1988.

Allara and Nuzzo, "Spontaneously Organized Molecular Assemblies. 1. Formation, Dynamics, and Physical Properties of n-Alkanoic Acids Adsorbed from Solution on an Oxidized Aluminum Surface," Langmuir 1:45-52, 1985.

Allara and Nuzzo, "Spontaneously Organized Molecular Assemblies. 2. Quantitative Infrared Spectroscopic Determination of Equilibrium Structures of Solution-Adsorbed n-Alkanoic Acids on an Oxidized Aluminum Surface," Langmuir 1 ; 52-66, 1985.

Bain and Whitesides, "Formation of Monolayers by the Coadsorption of Thiols on Gold: Variation in the Length of the Alkyl Chain," J. Am. Chem. Soc. 111:7164-7175, 1989.

Bain, et al., "Comparison of Self-Assembled Monolayers on Gold: Coadsorption of Thiols and Disulfides," Langmuir 5:723-727, 1989.

Bain, et al., "Formation of Monolayer Films by the Spontaneous Assembly of Organic Thiols from Solution onto Gold," J. Am. Chem. Soc. 111:321-335, 1989.

Bain, et al., "Formation of Monolayers by the Coadsorption of Thiols on Gold: Variation in the Head Group, Tail Group, and Solvent," J. Am. Chem. Soc. 111:7155-7164, 1989.

Bain, et al., "Strong Molecular Alignment in Anisotropic Fluid Media," Chem. Phys. Lett. 260:441-446, 1996.

Bawendi, et al., "Electronic Structure and Photoexcited-Carrier Dynamics in Nanometer-Size CdSe Clusters," Phys, Rev. Lett. 65:1623-1626, 1990.

Ba Wendi, et al., "X-ray Structural Characterization of Larger CdSe Semiconductor Clusters," J. Chem. Phys. 91:7282-7290, 1989.

Berry, et al., "Melting of Clusters and Melting," Phys. Rev. A 30:919-931, 1984.

Betzig and Chichester, "Single Molecules Observed by Near-Field Scanning Optical Microscopy," Science 262:1422-1425, 1993.

Bhargava, et al., "Quantum Confined Atoms of Doped ZnO Nanocrystals," *phys. stat. sol (b)* 229:897-901, 2002.

Bopp, et al., "Single-Molecule Spectroscopy With 27 fs Pulses: Time-Resolved Experiments and Direct Imaging Of Orientational Distributions," *Appl. Phys. Lett.* 73:7-9, 1998.

Braun, et al., "Electroluminescence and Electrical Transport in Poly(3-octylthiophene) Diodes," *J. Appl. Phys.* 72:564-568, 1992.

Brown, et al., "Poly(p-phenylenevinylene) Light-Emitting Diodes: Enhanced Electroluminescent Efficiency Through Charge Carrier Confinement," *Appl. Phys. Lett.* 61:2793-2795, 1992.

Bruchez, Jr., et al., "Semiconductor Nanocrystals as Fluorescent Biological Labels," *Science* 281:2013-2016, 1998.

Brus, "Zero-Dimensional 'Excitons' in Semiconductor Clusters," *IEEE J. Quantum Electronics* QE_22:1909-1914, 1987.

Brus, "A Simple Model for the Ionization Potential, Electron Affinity, and Aqueous Redox Potentials of Small Semiconductor Crystallites," *J. Chem. Phys.* 79:5566-5571, 1983.

Brus, "Electron-Electron and Electron-Hole Interactions in Small Semiconductor Crystallites: The Size Dependence of the Lowest Excited Electronic State," *J. Chem. Phys.* 80:4403-4409, 1984.

Brus, "Electronic Wave Functions in Semiconductor Clusters: Experiment and Theory," *J. Phys. Chem.* 90:2555-2560, 1986.

Buffat and Borel, "Size Effect on the Melting Temperature of Gold Particles," *Phys. Rev. A* 13:2287-2298, 1976.

Bunge, et al., "Growth and Morphology of Cadmium Chalcogenides: The Synthesis of Nanorods, Tetrapods, and Spheres from CdO and $Cd(O_2CCH_3)_2$," *J. Mater. Chem.* 13:1705-1709, 2003.

Byrne, et al., "Design of a Monomeric Arsinogallane and Chemical Conversion to Gallium Arsenide," *Science* 241:332-334, 1988.

Callomon, et al., "Rotational Analysis of the 2600 Angstrom Absorption System of Benzene," *Phil. Trans. R. Soc. Lond. A* 259:499-532, 1966.

Chamarro, et al., "Enhancement of Electron-Hole Exchange Interaction in CdSe Nanocrystals: A Quantum Confinement Effect," *Phys. Rev. B* 53:1336-1342, 1996.

Chamarro, et al., "Photoluminescence Polarization of Semiconductor Nanocrystals,"*J. Lumin.* 70:222-237, 1996.

Chan and Nie, "Quantum Dot Bioconjugates for Ultrasensitive Nonisotopic Detection," *Science* 281:2016-2018, 1998.

Chidsey and Loiacono, "Chemical Functionality in Self-Assembled Monolayers: Structural and Electrochemical Properties," *Langmuir* 6:682-691, 1990.

Chidsey, "Free Energy and Temperature Dependence of Electron Transfer at the Metal-Electrolyte Interface," *Science* 251:919-922, 1991.

Chidsey, et al., "Coadsorption of Ferrocene-Terminated and Unsubstituted Alkanethiols on Gold: Electroactive Self-Assembled Monolayers," *J. Am. Chem. Soc.* 112:4301-4306, 1990.

Colvin, et al., "Semiconductor Nanocrystals Covalently Bound to Metal Surfaces with Self-Assembled Monolayers," *J. Am. Chem. Soc.* 114:5221-5230, 1992.

Correa-Duarte, et al., "Stabilization of CdS Semiconductor Nanoparticles Against Photodegradation by Silica Coating Procedure," *Chem. Phys. Lett.* 286:497-501, 1998.

Dabbousi, et al., "Electroluminescence from CdSe Quantum-Dot/Polymer Composites," *Appl. Phys. Lett.* 66:1316-1318, 1995.

Dabbousi, et al., "(CdSe)ZnS Core-Shell Quantum Dots: Synthesis and Characterization of a Size Series of Highly Luminescent Nanocrystallites," *J. Phys. Chem. B* 101:9463-9475, 1997.

Dameron and Winge, "Characterization of Peptide-Coated Cadmium-Sulfide Crystallites," *Inorg. Chem.* 29:1343-1348, 1990.

Dickson, et al., "Simultaneous Imaging of Individual Molecules Aligned Both Parallel and Perpendicular to the Optic Axis," *Phys. Rev. Lett.* 81:5322-5325, 1998.

Edamatsu, et al., "Subpicosecond Dynamics of Confined Excitons and Optical Nonlinearities of CuCl Quantum Dots," *J. Lumin.* 66-67:406-409, 1996.

Efros, "Luminescence Polarization of CdSe Microcrystals,"*Phys. Rev. B* 46:7448-7458, 1992.

Efros, et al., "Band-Edge Exciton in Quantum Dots of Semiconductors With a Degenerate Valence Band: Dark and Bright Exciton States," *Phys. Rev. B* 54:4843-4856, 1996.

Ekimov, "Growth and Optical Properties of Semiconductor Nanocrystals in a Glass Matrix," *J. Lumin.* 70:1-20, 1996.

Ekimov, et al., "Growth of CdSe Nanocrystals in Ion-Implanted $SiO_2$ Films," *J. Cryst. Growth* 151:38-45, 1995.

Elghanian, et al., "Selective Colorimetric Detection of Polynucleotides Based on the Distance-Dependent Optical Properties of Gold Nanoparticles," *Science* 277:1078-1081, 1997.

Empedocles and Bawendi, "Quantum-Confined Stark Effect in Single CdSe Nanocrystallite Quantum Dots," *Science* 278:2114-2117, 1997.

Empedocles, et al., "Three-Dimensional Orientation Measurements of Symmetric Single Chromophores Using Polarization Microscopy," *Nature* 399:126-130, 1999.

Fox, et al., "Fluorescence and Redox Activity of Probes Anchored through an Aminotrithiol to Polycrystalline Gold," *Langmuir* 14:816-820, 1998.

Franceschetti, et al., "Many-Body Pseudopotential Theory of Excitons in InP and CdSe Quantum Dots," *Phys. Rev. B* 60:1819-1829, 1999.

Gan, et al., "Enhanced Photoluminescence and Characterization of Mn-Doped ZnS Nanocrystallites Synthesized in Microemulsion,"*Langmuir* 13:6427-6431, 1997.

Gao, et al., "In vivo Cancer Targeting and Imaging with Semiconductor Quantum Dots," *Nat. Biotechnol.* 22:969-976, 2004.

Goldstein, et al., "Melting in Semiconductor Nanocrystals," *Science* 256:1425-1427, 1992.

Green, et al., "Recent Advances in the Preparation of Semiconductors as Isolated Nanometric Particles: New Routes to Quantum Dots," *Chem. Commun.* 1999:2235-2241, 1999.

Guttler, et al., "Single Molecule Polarization Spectroscopy: Pentacene in p-Terphenyl," *Chem. Phys.* 211:421-430, 1996.

Ha, et al., "Single Molecule Dynamics Studied by Polarization Modulation," *Phys. Rev. Lett.* 77:3979-3982, 1996.

Hahn and Whetten, "Rigid-Fluid Transition in Specific-Size Argon Clusters," *Phys. Rev. Lett.* 61:1190-1193, 1988.

Han, et al., "Quantum-Dot-Tagged Microbeads for Multiplexed Optical Coding of Biomolecules," *Nat. Biotechnol.* 19:631-635, 1991.

Han, et al., "Synthesis of Gallium Nitride Nanorods Through a Carbon Nanotube-Confined Reaction," *Science* 277:1287-1289, 1997.

Hermann, et al., "Immunogold Labeling in Scanning Electron Microscopy," *Histochem. Cell Biol.* 106:31-39, 1996.

Hickman, et al., "Combining Spontaneous Molecular Assembly with Microfabrication to Pattern Surfaces: Selective Binding of Isonitriles to Platinum Microwires and Characterization by Electrochemistry and Surface Spectroscopy," *J. Am. Chem. Soc.* 111:7271-7272, 1989.

Hines and Guyot-Sionnest, "Synthesis and Characterization of Strongly Luminescing ZnS-Capped CdSe Nanocrystals," *J. Phys. Chem.* 100:468-471, 1996.

Honeycutt and Andersen, "Molecular Dynamics Study of Melting and Freezing of Small Lennard-Jones Clusters," *J. Phys. Chem.* 91:4950-4963, 1987.

Huynh, et al., "CdSe Nanocrystal Rods/Poly (3-hexylthiophene) Composite Photovoltaic Devices," *Adv. Mater.* 11:923-927, 1999.

Itoh, et al., "Subpicosecond Dynamics of Confined Excitons in CuCl Nanocrystals," *Mater. Sci. Eng. A Struct. Mater.* 217-218:167-170, 1996.

Itoh, et al., "Polaron and Exciton-Phonon Complexes in CuCl Nanocrystals," *Phys. Rev. Lett.* 74: 1645-1648, 1995.

Kabay, et al., "Removal of Metal Pollutants (Cd(II) and Cr (III)) from Phosphoric Acid Solutions by Chelating Resins Containing Phosphonic or Diphosphonic Groups," *Ind. Eng. Chem. Res.* 37:2541-2547, 1998.

Kagan, et al., "Long-Range Resonance Transfer of Electronic Excitations in Close-Packed CdSe Quantum-Dot Solids," *Phys. Rev. B* 54:8633-8643, 1996.

Klein, et al., "Scanned Probe Investigations of Chemically Derived Nanostructures," *Nanotechnology* 7:397-400, 1996.

Kneipp, et al., "Single Molecule Detection Using Surface-Enhanced Raman Scattering (SERS)," *Phys. Rev. Lett.* 78:1667-1670, 1997.

Kortan, et al., "Nucleation and Growth of CdSe on ZnS Quantum Crystallite Seeds, and Vice Versa, in Inverse Micelle Media," *J. Am. Chem. Soc.* 112:1327-1332, 1990.

Kovalev, et al., "Optically Induced Polarization Anisotrophy in Porous Si," *Phys. Rev. Lett.* 77:2089-2092, 1996.
Kuno, et al., "Magnetic Circular Dichroism Study of CdSe Quantum Dots," *J. Chem. Phys.* 108:4242-4247, 1998.
Kuno, et al., "The Band Edge Luminescence of Surface Modified CdSe Nanocrystallites: Probing the Luminescing State," *J. Chem. Phys.* 106:9869-9882, 1997.
Lacoste, et al., "Super Resolution Molecular Ruler Using Single Quantum Dots," *Biophys. J.* 78:402A, 2000.
Lawless, et al., "Bifunctional Capping of CdS Nanoparticles and Bridging to $TiO_2$," *J. Phys. Chem.* 99:10329-10335, 1995.
Lee, et al., "Full Color Emission from II-VI Semiconductor Quantum Dot-Polymer Composites," *Adv. Mater.* 12:1102-1105, 2000.
Lee, et al., "Adsorption of Ordered Zirconium Phosphonate Multilayer Films on Silicon and Gold Surfaces," *J. Phys. Chem.* 92:2597-2601, 1988.
Leppert, et al., "Structural and Optical Characteristics of ZnSe Nanocrystals Synthesized in the Presence of a Polymer Capping Agent," *Mater. Sci. Eng, B Solid State* 52:89-92, 1998.
Leung, et al., "Exicton Fine Structure in CdSe Nanoclusters," *Phys. Rev. B* 57:12291-12301, 1998.
Lieber, "One-Dimensional Nanostructures: Chemistry, Physics & Applications", *Solid State Commun.* 107:607-616, 1998.
Liu and Risbud, "Quantum-Dot Size-Distribution Analysis and Precipitation Stages in Semiconductor Doped Glasses," *J. Appl. Phys.* 68:28-32, 1990.
Lublinskaya, et al., "CdS Nanocrystal Growth in Thin Silica Films: Evolution of Size Distribution Function," *J. Cryst. Growth* 184-185:360-364, 1998.
Ludolph, et al., "Novel Single Molecule Precursor Routes for the Direct Synthesis of Highly Monodispersed Quantum Dots of Cadmium or Zinc Sulfide or Selenide," *Chem. Commun.* 1998:1849-1850, 1998.
Macklin, et al., "Imaging and Time-Resolved Spectroscopy of Single Molecules at an Interface," *Science* 272:255-258, 1996.
Malik, et al., "Semiconductor Nanoparticles: Their Properties, Synthesis and Potential for Application," *S. Air. J. Sci.* 96:55-60, 2000.
Maoz and Sagiv, "Penetration-Controlled Reactions in Organized Monolayer Assemblies. 1. Aqueous Permanganate Interaction with Monolayer and Multilayer Films of Long-Chaim Surfactants," *Langmuir* 3:1034-1044, 1987.
Maoz and Sagiv, "Penetration-Controlled Reactions in Organized Monolayer Assemblies. 2. Aqueous Permanganate Interaction with Self-Assembling Monolayer of Long-Chaim Surfactants," *Langmuir* 3:1045-1051, 1987.
Mattoussi, et al., "Self-Assembly of CdSe-ZnS Quantum Dot Bioconjugates Using an Engineered Recombinant Protein," *J. Am. Chem. Soc.* 122:12142-12150, 2000.
Mattoussi, et al., "Bioconjugation of Highly Luminescent Colloidal CdSe-ZnS Quantum Dots with an Engineered Two-Domain Recombinant Protein," *phys. stat. sol.* (b) 224:277-283, 2001.
Michael, et al., "Randomly Ordered Addressable High-Density Optical Sensor Arrays," *Anal. Chem.* 70:1242-1248, 1998.
Miller, et al., "Electroabsorption of Highly Confined Systems: Theory of the Quantum-Confined Franz-Keldysh Effect in Semiconductor Quantum Wires and Dots," *Appl. Phys. Lett.* 52:2154-2156, 1988.
Miller, et al., "Relation Between Electroabsorption in Bulk Semiconductors and in Quantum Wells: The Quantum-Confined Franz-Keldysh Effect," *Phys. Rev. B* 33:6976-6982, 1986.
Murray, et al., "Colloidal Synthesis of Nanocrystals and Nanocrystal Superlattices," *IBM J. Res. Dev.* 45:47-56, 2001.
Nirmal, et al., "Fluorescence Intermittency in Single Cadmium Selenide Nanocrystals," *Nature* 383:802-804, 1996.
Nirmal, et al., "Observation of the 'Dark Exciton' in CdSe Quantum Dots," *Phys. Rev. Lett.* 75:3728-3731, 1995.
Norris and Bawendi, "Measurement and Assignment of the Size-Dependent Optical Spectrum in CdSe Quantum Dots," *Phys. Rev. B* 53:16338-16346, 1996.
Norris, et al., "Size Dependence of Exciton Fine Structure in CdSe Quantum Dots," *Phys. Rev. B* 53:16347-16354, 1996.
Nuzzo and Allara, "Adsorption of Bifunctional Organic Disulfides on Gold Surfaces," *J. Am. Chem. Soc.* 105:4481-4483, 1983.
Nuzzo, et al., "Spontaneously Organized Molecular Assemblies. 3. Preparation and Properties of Solution Adsorbed Monolayers of Organic Disulfides on Gold Surfaces," *J. Am. Chem. Soc.* 109:2358-2368, 1987.
Olshavsky, et al., "Organometallic Synthesis of GaAs Crystallites Exhibiting Quantum Confinement," *J. Am. Chem. Soc.* 112:9438-9439, 1990.
Pale-Grosdemange, et al., "Formation of Self-Assembled Monolayers by Chemisorption of Derivatives of Oligo (ethylene glycol) of Structure $HS(CH_2)_{11}(OCH_2CH_2)$,OH on Gold," *J. Am. Chem. Soc.* 113:12-20, 1991.
Peng, et al., "Kinetics of II-VI and III-V Colloidal Semiconductor Nanocrystal Growth: 'Focusing' of Size Distributions," *J. Am. Chem. Soc.* 120:5343-5344, 1998.
Porter, et al., "Spontaneously Organized Molecular Assemblies. 4. Structural Characterization of n_Alkyl Thiol Monolayers on Gold by Optical Ellipsometry, Infrared Spectroscopy, and Electrochemistry," *J. Am. Chem. Soc.* 109:3559-3568, 1987.
Putvinski, et al., "Self-Assembly of Organic Multilayers with Polar Order Using Zirconium Phosphate Bonding Between Layers," *Langmuir* 6:1567-1571, 1990.
Ridley, et al., "All-Inorganic Field Effect Transistors Fabricated by Printing," *Science* 286:746-749, 1999.
Routkevitch, el al., "Electrochemical Fabrication of CdS Nanowire Arrays in Porous Anodic Aluminum Oxide Templates," *J. Phys. Chem.* 100:14037-14047, 1996.
Ruiter, et al., "Single Molecule Rotational and Translational Diffusion Observed by Near-Field Scanning Optical Microscopy," *J. Phys. Chem. A* 101:7318-7323, 1997.
Sandroff, et al., "GaAs Clusters in the Quantum Size Regime: Growth on High Surface Area Silica by Molecular Beam Epitaxy," *Science* 245:391-393, 1988.
Saviot, et al., "Size dependence of acoustic and optical vibrational modes of CdSe nanocrystals in glasses," *Journal of Non-Crystalline Solids* 197:238-246, 1996.
Saviot, et al., "Size-Selective Resonant Raman Scattering in CdS Doped Glasses," *Phys. Rev. B* 57:341-346, 1998.
Schlamp, et al., "Improved Efficiencies in Light Emitting Diodes Made with CdSe (CdS) Core/Shell Type Nanocrystals and a Semiconducting Polymer," *J. Appl. Phys.* 82:5837-5842, 1997.
Schmitt-Rink, et al.,"Theory of the Linear and Nonlinear Optical Properties of Semiconductor Microcrystallites," *Phys. Rev. B* 35:8113-8125, 1987.
Service, "Semiconductor Beacons Light Up Cell Structures" *Science* 281:1930-1931, 1998.
Sheng, et al., "Melting Transition of Small Molecular Clusters," *J. Phys. C* 14:L565-L569, 1981.
Shiang, et al., "Lattice Reorganization in Electronically Excited Semiconductor Clusters," *J. Chem. Phys.* 92:3232-3233, 1990.
Shiang, et al., "Symmetry of Annealed Wurtzite CdSe Nanocrystals: Assignment to the $C_{3v}$ Point Group," *J. Phys. Chem.* 99:17417-17422, 1995.
Sirenko, et al., "Spin-Flip and Acoustic-Phonon Raman Scattering in CdS Nanocrystals," *Phys. Rev. B* 58:2077-2087, 1998.
Smith, et al., "Measurement of Rotational Motion in Membranes Using Fluorescence Recovery After Photobleaching," *Biophys. J.* 36:73-91, 1981.
Strong and Whitesides, "Structures of Self-Assembled Monolayer Films of Organosulfur Compounds Adsorbed on Gold Single Crystals: Electron Diffraction Studies," *Langmuir* 4:546-558, 1988.
Tamulaitis, et al., "Dynamics of Nonlinear Optical Response of CuBr-Doped Glasses," *Superlattices and Microstructures* 13:199-202, 1993.
Tang, et al., "Electroluminescence of Doped Organic Thin Films," *J. Appl. Phys.* 65:3610-3616, 1989.
Tang and Vanslyke, "Organic Electroluminescent Diodes," *Appl. Phys. Lett.* 51:913-915, 1987.
Tillman, et al., "Oxidation of a Sulfide Group in a Self-Assembled Monolayer," *Langmuir* 5:1020-1026, 1989.
Tillman, et al., "Formation of Multilayers by Self-Assembly," *Langmuir* 5:101-111, 1989.

Tobin, et al., "Photoemission Investigation of Compound Semiconductor Monodisperse Clusters," *J. Vac. Sci. Technol. A* 9:852-853, 1991.

Ulman, et al., "Packing and Molecular Orientation of Alkanethiol Monolayers on Gold Surfaces," *Langmuir* 5:1147-1152, 1989.

Ulman and Tillman, "Self-Assembling Double Layers on Gold Surfaces: The Merging of Two Chemistries," *Langmuir* 5:1418-1420, 1989.

Valenta, et al., "Dynamics of Excitons in CuBr Nanocrystals: Spectral-Hole Burning and Transient Four-Wave-Mixing Measurements," *Phys. Rev. B* 57:1774-1783, 1998.

Wang, et al., "Large-Scale Identification, Mapping, and Genotyping of Single-Nucleotide Polymorphisms in the Human Genome," *Science* 280:1077-1082, 1998.

Wang, et al., "Synthesis and Characterization of MSe (M=Zn, Cd) Nanorods by a New Solvothermal Method," *Inorg. Chem. Commun.* 2:83-85, 1999.

Wasserman, et al., "Structure and Reactivity of Alkylsiloxane monolayers Formed by Reaction of Alkyltrichlorosilanes on Silicon Substrates," *Langmuir* 5:1074-1087, 1989.

Wasserman, et al., "The Structure of Self-Assembled Monolayers of Alkylsiloxanes on Silicon: A Comparison of Results from Ellipsometry and Low-Angle X-ray Reflectivity," *J. Am. Chem. Soc.* 111:5852-5861, 1989.

Wegener, "Fluorescence Recovery Spectroscopy as a Probe of Slow Rotational Motions," *Biophys. J.* 46:795-803, 1984.

Winzelar, et al., "Direct Allelic Variation Scanning of the Yeast Genome," *Science* 281:1194-1197, 1998.

Wu, et al., "Immunofluorescent Labeling of Cancer Marker Her2 and Other Cellular Targets with Semiconductor Quantum Dots," *Nat. Biotechnol.* 21:41-46, 2003.

Zen, et al., "Scanning Tunneling Microscopic Imaging of CdS Q Particles Prepared in Acetonitrile Solution," *Langmuir* 5:1355-1358, 1989.

Zhao and Fendler, "Semiconductor Particulate Films on Solid Supports," *Chem. Mater.* 3:168-174, 1991.

Zhao and Fendler, "Size Quantitization in Semiconductor Particulate Films," *J. Phys. Chem.* 95:3716-3723, 1991.

Haase, et al., "Photochemistry and Radiation Chemistry of Colloidal Semiconductors. 23. Electron Storage on ZnO Particles and Size Quantization," *J. Phys. Chem.* 92:482-487, 1988.

Jacoby, "Quantum Dots Meet Biomolecules," *Chem. Eng. News* 76:8, 1998.

Rubinstein, et al., "Ionic Recognition and Selective Response in Self-Assembling Monolayer Membranes on Electrodes," *Nature* 332:426-429, 1988.

U.S. Appl. No. 60/031,809, filed Jul. 29, 1996, C.A. Mirkin et al.

Aktsipetrov, O.A., et al. "Generation of reflected second harmonic at semiconductor quantum dots," *JETP Letters*, vol. 55, No. 8, 435-439 (1992).

Baltrameyunas, R., et al., "Fast switching of the transmission of light by glasses activated with CdS microcrystals," *Sov. Phys. Semicond.*, vol. 25 No. 2, 164-166 (1991).

Baltramiejunas, R., et al. "Rapid Processes of Darkening and Bleaching in CdS Doped Glasses," *Superlattices and Microstructures* vol. 10, No. 3, 307-310 (1990).

Chamarro, M., et al., "Enhancement of Exciton Exchange Interaction by Quantum Confinement in CdSe Nanocrystals," *Jpn. J. Appl. Phys*, vol. 34, 12-14 (1994).

Chamarro, M., et al., "Size-dependent Electron-Hole Exchange Interaction in CdSe Quantum Dots, *Il Nuovo Cimento*," vol. 17, Nos. 11-12, (1995) 1407-1412.

Chepic, D.I., et al., "Auger ionization of semiconductor quantum drops in a glass matrix," *Journal of Luminescence* 47 (1990) 113-127 North-Holland.

Efros, A.L., et al., "Resonance Raman Spectroscopy of Electron-Hole Pairs—Polar Phonon Coupling in Semiconductor Quantum Microcrystals," *Solid State Communications*, vol. 78, No. 10, pp. 853-856, 1991.

Ekimov, A. I., et al., "Absorportion and intensity-dependent photoluminescence measurements on CdSe quantum dots: assignment of the first electronic transitions," *Journal of the Optical Society of America*, vol. 10, Nos. 1-12, 100-107 (1992).

Ekimov, A.I., "Optical Properties of Oxide Glasses Doped by Semiconductor Nanocrystals." *Radiation Effects and Defects in Solids*, 1995, vol. 134, pp. 11-22.

Ekimov, A.I., "Optical Properties of Semiconductor Quantum Dots in Glass Matrix," *Physica Scripta.* vol. T39, 217-222 (1991).

Ekimov, A.I., et al. "Dimensional Effects in Luminescence Spectra of Zero-Dimensional Semiconductor Structures," *Bulletin of the Russian Academy of Sciences*, vol. 56, No. 2, pp. 154-157, Feb. 1992.

Ekimov, A.I., et al., "Spectra and Decay Kinetics of Radiative Recombination in CdS Microcrystals," *Journal of Luminescence* 46 (1990) 83-95 North-Holland.

Ekimov, A.I., et al., "Donor-like Exciton in Zero-Dimension Semiconductor Structures," *Solid State Communications*, vol. 69, No. 5, pp. 565-568, 1989.

Ekimov, A.I., et al., "Influence of high hydrostatic pressures on the exciton spectrum of CdS microcrystals in glass," *Sov. Phys. Semicond.* 23(9), Sep. 1989, pp. 965-966.

Ekimov, A.I., et al., "Nonlinear Optics of Semiconductor-Doped Glasses," *Phys. Stat. Sol.* (b) 150, (1988) pp. 627-633.

Ekimov, A.I., et al., "Optics of Zero Dimensional Semiconductor Systems, *Acta Physica Polonica A*," vol. 79 (1991), No. 1. pp. 5-14.

Ekimov, A.I., et al., "Photoluminescence of quasizero-dimensional semiconductor structures," *Sov. Phys. Solid State* 31(8), Aug. 1989, pp. 1385-1393.

Ekimov, A.I., et al., "Quantization of the energy spectrum of holes in the adiabatic potential of the electron," *JETP Lett.*, vol. 43, No. 6, Mar. 25, 1986, pp. 376-379.

Ekimov, A.I., et al., "Quantum Size Effect in Semiconductor Microcrystals," *Solid State Communications*, vol. 56, No. 11, pp. 921-924, 1985.

Ekimov, A.I., et al., "Quantum size effect in the optical spectra of semiconductor microcrystals," *Sov. Phys. Semicond.* 16(7), Jul. 1982, pp. 775-778.

Ekimov, A.I., et al., "Quantum size effect in three-dimensional microscopic semiconductor crystals," *JETP Lett*, vol. 34, No. 6, 20 Sep. 1981, pp. 345-349.

Ekimov, A.I., et al., "Quantum-Size Stark Effect in Semiconductor Microcrystals," *Journal of Luminescence* 46 (1990) 97-100 North-Holland.

Ekimov, A.I., et al., "Size quantization of the electron energy spectrum in a microscopic semiconductor crystal," *JETP Lett.*, vol. 40, No. 8, Oct. 25, 1984, pp. 1136-1139.

Grabovskis, V.Y., et al., "Photoionization of semiconducting microcrystals in glass," *Sov. Phys. Solid State* 31(1), Jan. 1989, pp. 149-151.

Gurevich, S.A., et al. "Preparation and investigation of $SIO_2$ films activated by CdS semiconductor nanocrystals," *Soviet Physics Semiconductors*, vol. 26, 57-59 (1992).

Gurevich, S.A., et al., "Growth of CdS nanocrystals in silicate glasses and in thin $SIO_2$ films in the Initial states of the phase separation of a solid solution," *Semiconductors*, 28 (5), May 1994, 486-493.

Itoh, T. et al., "Interface effects on the properties of confined excitons in CuC1 microcrystals," *Journal of Luminescence* 60 & 61 (1994) 396-399.

Itoh, T., et al., "Subpicosecond dynamics of confined excitons in CuC1 nanocrystals," *Materials Science and Engineering* A217/218 (1996) 167-170.

Jursenas, S., et al., "Surface Recombination of Nonequilibrium Electron-Hole Plasma in Laser-Modified Semiconductor-Doped Glasses," *Solid State Communications*, vol. 87, No. 6, 577-580 (1993).

Saviot, L., et al., "Effects of Resonance on Low-Frequency Raman Scattering From Semiconductor Nanocrystals," *Radiation Effects and Defects in Solids*, 1995, vol. 137, pp. 45-50.

Tamulaitis, G., et al., "Dynamics of Nonlinear Optical Response of CuBr-Doped Glasses," *Superlattices and Microstructures*, vol. 3, No. 2, 199-202 (1993).

Vandyshev, Y.V., et al., "Nonlinear optical properties of semiconductor microcrystals," *JETP Lett.*, vol. 46, No. 10, Nov. 25, 1987 pp. 435-439.

Volkov, A.S., et al., "Oscillations of polarization of recombination radiation of a variable gap semiconductor in a magnetic field," *JETP Lett.*, vol. 25 No. 55, 526-528 (1977).

Dneproviskii, V.S., et al., "Time-Resolved Luminescence of CdSe Microcrystals," *Solid State Communications*, vol. 74, No. 7, pp. 555-557, 1990.
Empedocles et al. "Photoluminescence Spectroscope of Single CdSe Nanocrystallite Quantum Dots" *Phys. Rev. Lett.* 77(18):3873 (Oct. 1996).
Gan et al. "Enhanced Photoluminescence and Characterization of Mn-Doped ZnS Nanocrystallites Synthesized in Microemulsion," *Langmuir* 1997(13):6427-6431 (1997).
Matsumoto et al. "Preparation of Monodisperse CdS Nanocrystals by Size Selective Photocorrosion" *J. Phys. Chem.* 100(32):13782 (Aug. 1996).
Mews et al., "Structural and spectroscopic investigations of CdS/HgS/CdS quantum-dot quantum wells," *Phys. Rev. B* 1996, 53, R13242-R13245.
Mićić et al., "Core-Shell Quantum Dots of Lattice-Matched ZnCdSe$_2$ Shells on InP Cores: Experiment and Theory," *J. Phys. Chem. B* 2000, 104 (51), 12149-12156.
Aggarwal et al., "Insights into US public biotech sector using patenting trends", 2006, Nature Biotechnology (vol. 24, No. 6, 643).
Beverloo et al., "Inorganic Phosphors as New Luminescent Labels for Immunocytochemistry and Time-Resolved Microscopy", 1990, Cytometry (vol. 11, pp. 784-792).
Bigham et al., "Deactivation of Q-CdS Photoluminescence Through Polynucleotide Surface Binding", 1992, Journal of Physical Chemistry (vol. 96, pp. 10581-10583).
Bigham et al., "The Influence of Adenine Content on the Properties of Q-CdS Clusters Stabilized by Polynucleotides", 1995, Colloids and Surfaces A: Physicochemical and Engineering Aspects (vol. 95, pp. 211-219).
Bigham, "Influence of Polynucleotide Stabilizers on Selected Properties of Quantum-Confined Cadmium Sulfide Semiconductor Clusters", 1996, Thesis submitted to Graduate Faculty of AddRan College of Arts and Sciences Texas Christian University.
Bimberg et al., "Luminescence properties of semiconductor quantum dots", 1997, J. Luminescence (vol. 72-74. ppp. 34-37).
Chamarro et al., "Optical properties of Mn-doped CdS nanocrystals", 1996, J. of Crystal Growth (vol. 159, pp. 853-856).
Chandler et al., "Preparation and Spectroscopic Analysis of Semiconductor Colloids", 1993, Journal of Chemical Education (vol. 70, A7-A10).
Chikan et al., "Synthesis of highly luminescent GaSe nanoparticles", 2002, Nano Letters (vol. 2, No. 2, 141-145).
Coffer et al., "Dictation of the Shape of Mesoscale Semiconductor Nanoparticles Assemblies by Plasmid DNA", 1996, Applied Physics Letter (vol. 69(25), pp. 3851-3853).
Coffer et al., "Nucleotides As Structural Templates for the Self-Assembly of Quantum-Confined CdS Clusters", 1991, R.R. Material Research Society Symposium Proceedings, (Issue 206, pp. 527-531).
Dameron et al., "Biosynthesis of Cadmium Sulphide Quantum Semiconductor Crystallites", 1989, Nature (vol. 338,pp. 596-597).
Dameron et al., "Glutathione-Coated Cadmium Sulfide Crystallites in *Candida glabrata*", 1989, The Journal of Biological Chemistry (vol. 264(29), pp. 17355-17360).
Gelbart et al., "The 'New' science of 'complex fluids'", 1996, J. Phys. Chem. (vol. 100, pp. 13169-13189).
Harrison et al., "Wet chemical synthesis of highly luminescent HgTe/CdS core/shell nanocrystals", 2000, Adv. Mater. (vol. 12, No. 2, 123).
Haugland, "Handbook of Fluorescent Probes and Research Chemicals", 1996, Molecular Probes (Sixth edition).
Hermanson, "Bioconjugate Techniques", 1996, Academic Press (New York).
Huang et al., "Assembly and applications of the inorganic nanocrystals in polymer networks", 1998, Thin Solid Films (vol. 327-329, pp. 536-540).
Huibers et al., "Prediction of critical micelle concentration using a quantitative structure-property relationship approach. 1. Nonionic surfactants", 1996, Langmuir (vol. 12, pp. 1462-1470).
Lawton et al., "Biomolecular Self-Assembly of Quantum Dot Composites", 1994, Materials Research Symposium Proceedings vol. 330 (Biomolecular Materials by Design), pp. 283-288.
Mirkin et al., "A DNA-based method for rationally assembling nanoparticles into macroscopic materials", 1996, Nature (vol. 382, pp. 607-609).
Moffitt et al., "Spherical assemblies of semiconductor nanoparticles in water-soluble block copolymer aggregates", 1998, Chem. Mater. (vol. 10, pp. 1021-1028).
Ohnishi, "Electroluminescent display materials", 1989, Annu. Rev. Mater. Sci. (vol. 19, pp. 83-101).
Olshavsky et al., "Synthesis of CdS nanoparticles in solution and in a polyphosphazene matrix", 1997, Chem. Mater. (vol. 9, pp. 1367-1376).
Pileni et al., "Synthesis of Cadmium sulfide in situ in reverse micelles: influence of the preparation modes on size, polydispersity, and photochemical reactions", 1992, Chem. Mater. (vol. 4, pp. 338-345).
Qiu et al., "Study of the core-shell nanoparticle formed through the 'coil-to-globule' transition of poly(N-isopropylacrylamide) grafted with poly(ethylene oxide)", 1997, Macromolecules (vol. 30, pp. 7921-7926).
Rogach et al., "Layer-by-layer assembled films of HgTe nanocrystals with strong infrared emission", 2000, Chem. Mater. (vol. 12, pp. 1526-1528).
Service, "Materials Science: Small Clusters hit the big time", 1996, Science (vol. 271, pp. 920-922).
Taiapin et al., "PbSe nanocrystal solids for n- and p-channel thin film field-effect transistors", 2005, Science (vol. 310, pp. 86-89).
Toth et al., "Structure of BRIJ-35 nonionic surfactant in water: a reverse monte carlo study", 2006, Langmuir (vol. 22, pp. 590-597).
Watzke et al., "Quantum size effects of in situ generated colloidal CdS particles in Dioctadecyldimethylammonium chloride surfactant vesicles", 1987, J. Phys. Chem. (vol. 91, pp. 854-861).
Weller et al., "Nanocrystals of II-V1 Semiconductor Materials", 1995, Materials Research Symposium Proceedings vol. 358 (Microcrystalline and Nanocrystalline Semiconductors), pp. 213-218.
Weller, "Optical Properties of Quantized Semiconductor Particles", 1996, Philosophical Transactions of the Royal Society: A. (vol. 354(1708), pp. 757-766).
Yang et al., "Epitaxial growth of size-quantized cadmium sulfide crystals under arachidic acid monolayers", 1995, J. Phys. Chem. (vol. 99, pp. 5500-5504).
Mikulec, F.V. et al., Synthesis and characterization of highly luminescent (CdSe)ZnS quantum dots: Advances in microcrystalline and nanocrystalline semiconductors, Symposium 1996, Boston, MA, Mater. Res. Soc. 1997, Pittsburgh, PA, USA, Dec. 2-6, 1996, pp. 359-364.
Murray, C. B., "Synthesis and characterization of II-IV quantum dots and their assembly into 3D quantum dot superlattices." 1995. Thesis.
Alivisatos, "Semiconductor Clusters, Nanocrystals, and Quantum Dots," *Science*, 271:933-937, Feb. 16, 1996.
Alivisatos et al., "Organization of 'nanocrystal molecules' using DNA", *Nature*, 382:609-611, Aug. 15, 1996.
Baldwin et al., "Synthesis of a Small Molecule Combinatorial Library Encoded with Molecular Tags," *J. Am. Chem. Soc.*, 117:5588-5589, 1995.
Bawendi et al., "Luminescence properties of CdSe quantum crystallites: resonance between interior and surface localized states," *J. Chem. Phys.*, 96(2):946-954, Jan. 15, 1992.
Beverloo et al., "Preparation and Microscopic Visualization of Multicolor Luminescent Immunophosphors," *Cytometry*, 13:561-570, 1992.
Chee et al., "Accessing Genetic Information with High-Density DNA Arrays" *Science*, 274(5287):610-614, Oct. 25, 1996.
Coffer et al., "Characterization of quantum-confined CdS Nanocrystallites stabilized by deoxyribonucleic acid (DNA)" *Nanotechnology*, 3:69-76, 1992.
Colvin et al., "Light-emitting diodes made from cadmium selenide nanocrystals and a semiconducting polymer" *Nature*, 370(6488):354-357, Aug. 4, 1994.
Cook, "Scintillation proximity assay: a versatile high-throughput screening technology," *Drug Discovery Today*, 1(7):287-294, Jul. 1996.
Czarnik, "Encoding methods for combinatorial chemistry" *Curr Opin Chem Biol.*, 1(1):60-66, Jul. 1996.
Danek et al., "Synthesis of Luminescent Thin-Film CdSe/ZnSe Quantum Dot Composites Using CdSe Quantum Dots Passivated with an Overlayer of ZnSe" *Chem. Mater.*,8(1):173-180, 1996.
Egner et al., "Tagging in combinatorial chemistry: the use of coloured and fluorescent bads" *Chem. Commun.*, 735-736, Apr. 21, 1997.
Fodor, "Techwire" *Science*, 277(5324):393-395, Jul. 18, 1997.
Guha et al., "Hybrid organic-inorganic semiconductor-based light-emitting diodes" *J. Appl. Phys.*, 82(8):4126-4128, Oct. 15, 1997.

Jarvis et al., "Solution Synthesis and Photoluminescence Studies of Small Crystallites of Cadmium Telluride," *Mat. Res. Soc. Symp. Proc.*, 272:229-234, 1992.

Kagan et al., "Electronic Energy Transfer in CdSe Quantum Dot Solids," *Physical Review Letters*, 76(9):1517-1520, Feb. 26, 1996.

Kagan et al., "Long-range resonance transfer of electronic excitations in close-packed CdSe quantum-dot solids," *Physical Review B*, 54(12):8633-8643, Sep. 15, 1996-II.

Lee et al., "Surface Derivatization of Nanocrystalline CdSe Semiconductors," *Mat. Res. Soc. Symp. Proc.*, 452:323-328, Mar. 13, 1997.

Liz-Marzan et al., "Synthesis of Nanosized Gold-Silica Core-Shell Particles" *Langmuir*, 12(18):4329-4335, 1996.

Mahtab et al., "Protein-Sized Quantum Dot Luminescence Can Distinguish between 'Straight', 'Bent', and 'Kinked' Oligonucletides", *J. Am. Chem. Soc.*, 117:9099-9100, 1995.

Mahtab et al., "Preferential-Absorption of a 'Kinked' DNA to a Neutral Curved Surface: Comparison to and Implications for Nonspecific DNA-Pprotein Interactions," *J. Am. Chem. Soc.*, 118(30):7028-7032, 1996.

McGall et al., "Light-directed synthesis of high-density oligonucleotide arrays using semiconductor photoresists" *Proc. Natl. Acad. Sci. USA*, 93:13555-13560, Nov. 1996.

Moran et al., "Radio Frequency Tag Encoded Combinatorial Library Method for the Discovery of Tripeptide-Substituted Cinnamic Acid Inhibitors of the Protein Tyrosine Phosphatase PTP1B" *J. Am. Chem. Soc.*, 117:10787-10788, 1995.

Müllenborn et al., "Characterization of Solution-Synthesized CdTe and HgTe," *Applied Physics*, 56:317-321, 1993.

Murphy et al., "Quantum Dots as Inorganic DNA-Binding Proteins," *Mat. Res. Soc. Symp.*, 452:597-600, Mar. 13, 1997.

Nicolaou et al., "Radiofrequency Encoded Combinatorial Chemistry" *Ingew. Chem. Int. Ed. Engl.*, 34(20):2289-2291, 1995.

Pehnt et al., "Nanoparticle precursor route to low-temperature spray deposition of CdTe thin films," *Appl. Phys. Lett.*, 67(15):2176-2178, Oct. 1995.

Peng et al., "Epitaxial Growth of Highly Luminescent CdSe/CdS Core/Shell Nanocrystals with Photostability and Electronic Accessibility," *J. Am. Chem. Soc.*, 119(30):7019-7029, 1997.

Peng et al., "Synthesis and Isolation of a Homodimer of Cadmium Selenide Nanocrystals," *Angew. Chem. Int. Ed. Engl.*, 36(112):145-147, 1997.

Plunkett et al., "Combinatorial Chemistry and New Drugs" *Sci Am.*, 276(4):68-73, Apr. 1997.

Rogach et al., "Synthesis and Characterization of Thiol-Stabilized CdTe Nanocrystals" *Ber. Bunsenges. Phys. Chem.*, 100(11):1772-1778, Nov. 1996.

Schröck et al., "Multicolor Spectral Karyotyping of Human Chromosomes," *Science*, 273:494-497, Jul. 26, 1996.

Spanhel et al., "Photochemistry of Colloidal Semiconductors. Surface Modification and Stability of Strong Luminescing CdS Particles" *J. Am. Chem. Soc.*, 109(19):5649-5655, 1987.

Steigerwald et al., "Surface Derivatization and Isolation of Semiconductor Cluster Molecules," *J. Am. Chem. Soc.*, 110:3046-3050, 1988.

Whitesell et al., "Directionally Aligned Helical Peptides on Surfaces" *Science*, 261:73-76, Jul. 2, 1993.

C.B. Murray et al.; "Synthesis and Characterization of Nearly Monodisperse CdE (E=S,Se,Te) Semiconductor Nanocrystallites"; *J. Am. Chem. Soc* 115; pp. 8709-8715 (1993).

Database Crossfire Online!; Beilstein Institut zur Forderung der Chemischen Wissenschaft; Beilstein Registry Nos. 2097823 and 1860016; XP002152687—Abstract.

International Search Report (partial) dated Nov. 30, 2000.

"Strongly Photoluminescent CdTe Nanocrystals by Proper Surface Modification," M. Gao et al., *J. Phys. Chem. B*. 102:8360-8363 (1998).

"Photochemistry and Radiation Chemistry of Colloidal Semiconductors. 33. Chemical Changes and Fluorescence in CdTe and ZnTe," U. Resch et al., *Langmuir* 5:1015-1020 (1989).

"An EXAFS Study on Thiolcapped CdTe Nanocrystals," J. Rockenberger et al., *Ber. Bunsenges. Phys. Chem.* 102:1561-1564 (1998).

"Synthesis, Morphology and Optical Properties of Thiol-Stabilized CdTe Nanoclusters in Aqueous Solution," A. L. Rogach et al., *Ber. Bunsenges. Phys. Chem.* 101:1668-1670 (1997).

"Micro photoluminescence spectra of CdTe and CdMnTe self-organized quantum dots," T. Kuroda et al., *Journal of Luminescence* 83-84:321-342 (1999).

"Quantum confinement effects on the optical phonons of CdTe quantum dots," A.M. De Paula et al., *Superlattices and Microstructures* 23:1103-1106 (1998).

"Probing of the quantum dot size distribution in CdTe-doped glasses by photoluminescence excitation spectroscopy," C.R.M. de Oliveira et al., *Appl. Phys. Lett.* 66:439-441 (1995).

"Synthesis and Characterization of Thiol-Stabilized CdTe Nanocrystals," A.L. Rogach et al., *Ber. Bunsenges. Phys. Chem.* 100:1772-1778 (1996).

"Synthesis and Characterization of Surface-Modified Colloidal CdTe Quantum Dots," T. Rajh et al., *J. Phys. Chem.* 97:11999-12003 (1993).

"Nanoparticle precursor route to low-temperature spray deposition of CdTe thin films," M. Pehnt et al., *Appl. Phys. Lett.* 67:2176-2178 (1995).

"Characterization of Solution-Synthesized CdTe and HgTe," M. Müllenborn et al., *Applied Physics* A56:317-321 (1993).

"Solution Synthesis and Photoluminenscence Studies of Small Crystallites of Cadmium Telluride," R. F. Jarvis, Jr. et al., *Mat. Res. Soc. Symp. Proc.*, 272:229-235 (1992).

Loher et al., "Epitaxy films of the 3D semiconductor CdS on the 2D layered substrate MX2 prepared by Van der Waals epitaxy" Journal of Crystal Growth, vol. 146, 1995, pp. 408-412.

Tsuji et al., "Characterization of CdS thin film in high efficient CdS/CdTe solar cells", Journal of Crystal Growth, vol. 214/215, 2000, pp. 1142-1147.

Danek et al., "Preparation of II-VI quantum dot composites by electrospray organometallic chemical vapor deposition." Journal of Crystal Growth, vol. 145 (1994), p. 714-720.

Notice of Intent to Issue Ex Parte Reexamination Certificate mailed Oct. 1, 2010.

Ashwood et al., "Synthesis and Antihypertensive Activity of 4-(Substituted-carbonylamino)-2H-1-benzppyrans" J. Med. Chem., 33_2667-2672 (1990).

Bruchez, "Luminescent Semiconductor Nanocrystals: Intermittent Behavior and Use as Fluorescent Biological Probes" Ph.D. dissertation, University of California, Dec. 17, 1998.

Bruchez et al., "Semiconductor Nanocrystals as Fluorescent Biological Labels" Science, 281:2013-2016 (Sep. 25, 1998).

Chandler et al., "Spectroscopic Analysis of Semiconductor Colloids" Journal of Chemical Education, 70:A7-A10 (Jan. 1993).

Leff "Color-coding Quantum Dots Debut with Promising Careers in Clinical Diagnostics Field," Bioworld Today, copied from the internet as pp. 1-2 (Sep. 25, 1998).

Zhang et al., "Novel Flow Cytometry Compensation Standards: Internally Stained Fluorescent Microspheres with Matched Emission Spectra and Long-Term Stability" Cytometry, 33:244-248 (1998).

U.S. Patent No. 6,322,901 (Reexamination Control No. 90/010,736)—Office Action dated Dec. 24, 2009.

U.S. Patent No. 6,861,155 (Reexamination Control No. 95/001,268)—Request for Reexamination and accompanying documents and Office Action dated Feb. 4, 2010.

U.S. Patent No. 7,125,605 (Reexamination Control No. 95/001,298)—Request for Reexamination and accompanying documents.

*Invitrogen Corporation, Quantum Dot Corporation, Molecular Probes, Inc and Regents of the University of California v. Evident Technologies, Inc.*, and Does 1 through 5, Inclusive, Civil Action 6:08-cv-163-LD—Defendants' Invalidity Contentions.

\* cited by examiner

HIGHLY LUMINESCENT COLOR-SELECTIVE NANOCRYSTALLINE MATERIALS

CLAIM OF PRIORITY

This application is a continuation of U.S. patent application Ser. No. 12/509,869, filed Jul. 27, 2009, which is a continuation of U.S. patent application Ser. No. 11/502,493, filed on Aug. 11, 2006, now U.S. Pat. No. 7,566,476, which is a divisional of U.S. patent application Ser. No. 10/960,947, filed Oct. 12, 2004, which is a continuation of U.S. patent application Ser. No. 10/642,578, filed on Aug. 19, 2003, now U.S. Pat. No. 6,861,155, which is a continuation of U.S. patent application Ser. No. 09/625,861, filed on Jul. 26, 2000, now U.S. Pat. No. 6,607,829, which claims priority to U.S. Patent Application Ser. No. 60/145,708, filed on Jul. 26, 1999, and is a continuation-in-part of U.S. patent application Ser. No. 08/969,302, filed Nov. 13, 1997, now U.S. Pat. No. 6,322,901, each of which is hereby incorporated by reference.

FEDERALLY SPONSORED RESEARCH OR DEVELOPMENT

This invention was made with government support under Contract No. DMR-94-00334 from the National Science Foundation. The government has certain rights in the invention.

FIELD OF THE INVENTION

This invention relates to luminescent nanocrystalline materials which emit visible light over a very narrow range of wavelengths. The invention further relates to materials which emit visible light over a narrow range tunable over the entire visible spectrum.

BACKGROUND OF THE INVENTION

Semiconductor nanocrystallites (quantum dots) whose radii are smaller than the bulk exciton Bohr radius constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of quantum dots shift to the blue (higher energies) as the size of the dots gets smaller.

Bawendi and co-workers have described a method of preparing monodisperse semiconductor nanocrystallites by pyrolysis of organometallic reagents injected into a hot coordinating solvent (J. Am. Chem. Soc., 115:8706 (1993)). This permits temporally discrete nucleation and results in the controlled growth of macroscopic quantities of nanocrystallites. Size selective precipitation of the crystallites from the growth solution provides crystallites with narrow size distributions. The narrow size distribution of the quantum dots allows the possibility of light emission in very narrow spectral widths.

Although semiconductor nanocrystallites prepared as described by Bawendi and co-workers exhibit near monodispersity, and hence, high color selectivity, the luminescence properties of the crystallites are poor. Such crystallites exhibit low photoluminescent yield, that is, the light emitted upon irradiation is of low intensity. This is due to energy levels at the surface of the crystallite which lie within the energetically forbidden gap of the bulk interior. These surface energy states act as traps for electrons and holes which degrade the luminescence properties of the material.

In an effort to improve photoluminescent yield of the quantum dots, the nanocrystallite surface has been passivated by reaction of the surface atoms of the quantum dots with organic passivating ligands, so as to eliminate forbidden energy levels. Such passivation produces an atomically abrupt increase in the chemical potential at the interface of the semiconductor and passivating layer (See, A. P. Alivisatos, J. Phys. Chem. 100:13226 (1996)). Bawendi et al. (J. Am. Chem. Soc., 115:8706 (1993)) describe CdSe nanocrystallites capped with organic moieties such as tri-n-octyl phosphine (TOP) and tri-n-octyl phosphine oxide (TOPO) with quantum yields of around 5-10%.

Passivation of quantum dots using inorganic materials also has been reported. Particles passivated with an inorganic coating are more robust than organically passivated dots and have greater tolerance to processing conditions necessary for their incorporation into devices. Previously reported inorganically passivated quantum dot structures include CdS-capped CdSe and CdSe-capped CdS (Tian et al., J. Phys. Chem. 100:8927 (1996)); ZnS grown on CdS (Youn et al., J. Phys. Chem. 92:6320 (1988)); ZnS on CdSe and the inverse structure (Kortan et al., J. Am. Chem. Soc. 112:1327 (1990)); and $SiO_2$ on Si (Wilson et al., Science 262:1242 (1993)). These reported quantum dots exhibit very low quantum efficiency and hence are not commercially useful in light emitting applications.

M. A. Hines and P. Guyot-Sionnest report the preparation of ZnS-capped CdSe nanocrystallites which exhibited a significant improvement in luminescence yields of up to 50% quantum yield at room temperature (J. Phys. Chem. 100:468 (1996)). However, the quality of the emitted light remained unacceptable because of the large size distribution of the core of the resulting capped nanocrystallites.

Danek et al. report the electronic and chemical passivation of CdSe nanocrystals with a ZnSe overlayer (Chem. Materials 8:173 (1996)). Although it might be expected that such ZnSe-capped CdSe nanocrystallites would exhibit as good as or better quantum yield than the ZnS analogue due to the better unit cell matching of ZnSe, in fact, the resulting material showed only disappointing improvements in quantum efficiency ($\leq 0.4\%$ quantum yield).

Thus there remains a need for semiconductor nanocrystallites capable of light emission with high quantum efficiencies throughout the visible spectrum, which possess a narrow particle size (and hence with narrow photoluminescence spectral range).

It is the object of the invention to provide semiconductor nanocrystallites which overcome the limitations of the prior art and which exhibit high quantum yields with photoluminescence emissions of high spectral purity.

SUMMARY OF THE INVENTION

In one aspect of the invention, a coated nanocrystal capable of light emission includes a substantially monodisperse core selected from the group consisting of CdX, where X=S, Se, Te; and an overcoating of ZnY, where Y=S, Se, and mixtures thereof uniformly deposited thereon, said coated core characterized in that when irradiated the particles emit light in a narrow spectral range of no greater than about 40 nm at full width half max (FWHM). In some embodiments, the narrow spectral range is selected from the spectrum in the range of about 470 nm to about 620 nm and the particle size of the core is selected from the range of about 20 Å to about 125 Å.

In other embodiments of the invention, the coated nanocrystal is characterized in that the nanocrystal exhibits less than a 10% and preferably less than 5%, rms deviation in diameter of the core. The nanocrystal preferably exhibits photoluminescence having quantum yields of greater than 30%, and most preferably in the range of about 30 to 50%.

In another embodiment of the invention, the overcoating comprises one to two monolayers of ZnY. The nanocrystal may further comprise an organic layer on the nanocrystal outer surface. The organic layer may be comprised of moieties selected to provide compatibility with a suspension medium, such as a short-chain polymer terminating in a moiety having affinity for a suspending medium, and moieties which demonstrate an affinity to the quantum dot surface. The affinity for the nanocrystal surface promotes coordination of the organic compound to the quantum dot outer surface and the moiety with affinity for the suspension medium stabilizes the quantum dot suspension.

In another aspect of the invention, a method of preparing a coated nanocrystal capable of light emission includes introducing a substantially monodisperse first semiconductor nanocrystal and a precursor capable of thermal conversion into a second semiconductor material into a coordinating solvent. The coordinating solvent is maintained at a temperature sufficient to convert the precursor into the second semiconductor material yet insufficient to substantially alter the monodispersity of the first semiconducting nanocrystal and the second semiconductor material has a band gap greater than the first semiconducting nanocrystal. An overcoating of the second semiconductor material is formed on the first semiconducting nanocrystal.

In one embodiment of the invention, the monodispersity of the nanocrystal is monitored during conversion of the precursor and overcoating of the first semiconductor nanocrystal. In another embodiment, an organic overcoating is present on the outer nanocrystal surface, obtained by exposing the nanocrystal to an organic compound having affinity for the nanocrystal surface, whereby the organic compound displaces the coordinating solvent.

In addition to having higher quantum efficiencies, ZnS overcoated particles are more robust than organically passivated nanocrystallites and are potentially more useful for optoelectronic devices. The (CdSe)ZnS dots of the invention may be incorporated into electroluminescent devices (LEDs). In addition, the (CdSe)ZnS dots of the invention may exhibit cathodoluminescence upon excitation with both high and low voltage electrons and may be potentially useful in the production of alternating current thin film electroluminescent devices (ACTFELD). In the naming convention used herein to refer to capped nanocrystallites, the compound found within parentheses represents the core compound (i.e. the bare "dot"), while the compound which follows represents the overcoated passivation layer.

These and other features and advantages of the invention are set forth in the description of the invention, which follows.

DETAILED DESCRIPTION OF THE INVENTION

Figure 1:
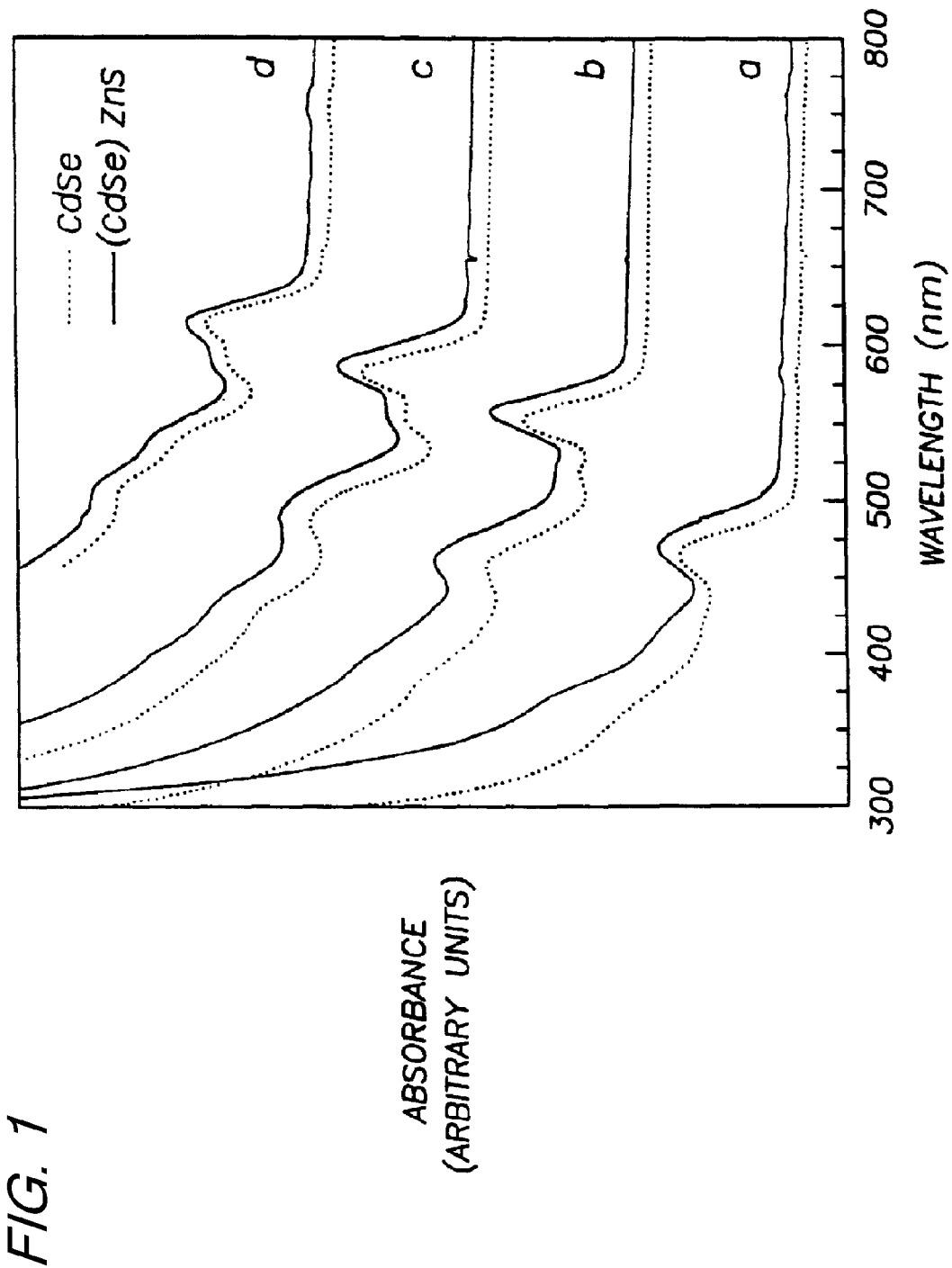
FIG. 1 shows the absorption spectra of CdSe dots with diameters measuring (a) 23 Å, (b) 42 Å, (c) 48 Å and (d) 55 Å before (dashed lines) and after (solid lines) overcoating with 1-2 monolayers of ZnS.

The present invention is directed to the preparation of a series of room temperature, highly luminescent ZnS-capped CdSe ((CdSe)ZnS) nanocrystallites having a narrow particle size distribution. Nanocrystallites of the present invention exhibit high quantum yields greater than about 30% and preferably in the range of about 30-50% and a narrow band edge luminescence spanning most of the visible spectrum from 470 nm to 625 nm. The core of the nanocrystallites is substantially monodisperse. By monodisperse, as that term is used herein, it is meant a colloidal system in which the suspended particles have substantially identical size and shape. For the purposes of the present invention, monodisperse particles deviate less than 10% in rms diameter in the core, and preferably less than 5% in the core.

When capped quantum dots of the invention are illuminated with a primary light source, a secondary emission of light occurs of a frequency that corresponds to the band gap of the semiconductor material used in the quantum dot. As previously discussed, the band gap is a function of the size of the nanocrystallite. As a result of the narrow size distribution of the capped nanocrystallites of the invention, the illuminated quantum dots emit light of a narrow spectral range resulting in high purity light. Spectral emissions in a narrow range of no greater than about 60 nm, preferably 40 nm and most preferably 30 nm at full width half max (FWHM) are observed.

The present invention also is directed to a method of making capped quantum dots with a narrow particle size distribution. The capped quantum dots of the invention may be produced using a two step synthesis in which a size selected nanocrystallite is first synthesized and then overcoated with a passivation layer of a preselected thickness. In preferred embodiments, processing parameters such as reaction temperature, extent of monodispersity and layer thickness may be monitored during crystal growth and overcoating to provide a coated quantum dot of narrow particle size distribution, high spectral purity and high quantum efficiency. "Quantum yield" as that term is used herein, means the ratio of photons emitted to that absorbed, e.g., the photoluminescence quantum yield.

The method is described for a (CdSe)ZnS quantum dot, but it is understood that the method may be applied in the preparation of a variety of known semiconductor materials. The first step of a two step procedure for the synthesis of (CdSe)ZnS quantum dots involves the preparation of nearly monodisperse CdSe nanocrystallites. The particles range in size from about 23 Å to about 55 Å with a particle size distribution of about 5-10%. These dots are referred to as "bare" dots. The CdSe dots are obtained using a high temperature colloidal growth process, followed by size selective precipitation.

The high temperature colloidal growth process is accomplished by rapid injection of the appropriate organometallic precursor into a hot coordinating solvent to produce a temporally discrete homogeneous nucleation. Temporally discrete nucleation is attained by a rapid increase in the reagent concentration upon injection, resulting in an abrupt supersaturation which is relieved by the formation of nuclei and followed by growth on the initially formed nuclei. Slow growth and annealing in the coordinating solvent results in uniform surface derivatization and regularity in the core structure.

Injection of reagents into the hot reaction solvent results in a short burst of homogeneous nucleation. The depletion of reagents through nucleation and the sudden temperature drop associated with the introduction of room temperature reagents prevents further nucleation. The solution then may be gently heated to reestablish the solution temperature. Gentle reheating allows for growth and annealing of the crystallites. The higher surface free energy of the small crystallites makes them less stable with respect to dissolution in the solvent than larger crystallites. The net result of this stability gradient is the slow diffusion of material from small particles to the surface of large particles ("Ostwald ripening"). Growth of this kind results in a highly monodisperse colloidal suspension from systems which may initially be highly polydisperse.

Both the average size and the size distribution of the crystallites in a sample are dependent on the growth temperature. The growth temperature necessary to maintain steady growth increases with increasing average crystal size. As the size distribution sharpens, the temperature may be raised to maintain steady growth. As the size distribution sharpens, the temperature may be raised in 5-10° C. increments to maintain steady growth. Conversely, if the size distribution begins to spread, the temperature may be decreased 5-10° C. to encourage Ostwald ripening and uniform crystal growth. Generally, nanocrystallites 40 Angstroms in diameter can be grown in 2-4 hours in a temperature range of 250-280° C. Larger samples (60 Angstroms or more) can take days to grow and require temperatures as high as 320° C. The growth period may be shortened significantly (e.g., to hours) by using a higher temperature or by adding additional precursor materials.

Size distribution during the growth stage of the reaction may be approximated by monitoring the absorption line widths of the particles. Modification of the reaction temperature in response to changes in the absorption spectrum of the particles allows the maintenance of a sharp particle size distribution during growth. It is also contemplated that reactants could be added to the nucleation solution during crystal growth to grow larger crystals.

The particle size distribution may be further refined by size selective precipitation. In a preferred embodiment, this may be accomplished by manipulation of solvent composition of the nanocrystallite suspension.

The CdSe nanocrystallites are stabilized in solution by the formation of a lyophilic coating of alkyl groups on the crystallite outer surface. The alkyl groups are provided by the coordinating solvent used during the growth period. The interparticle repulsive force introduced by the lyophilic coating prevents aggregation of the particles in solution. The effectiveness of the stabilization is strongly dependent upon the interaction of the alkyl groups with the solvent. Gradual addition of a non-solvent will lead to the size-dependent flocculation of the nanocrystallites. Non-solvents are those solvents in which the groups which may be associated with the crystallite outer surface show no great affinity. In the present example, where the coordinating group is an alkyl group, suitable non-solvents include low molecular weight alcohols such as methanol, propanol and butanol. This phenomenon may be used to further narrow the particle size distribution of the nanocrystallites by a size-selective precipitation process. Upon sequential addition of a non-solvent, the largest particles are the first to flocculate. The removal of a subset of flocculated particles from the initial solution results in the narrowing of the particle size distribution in both the precipitate and the supernatant.

A wealth of potential organometallic precursors and high boiling point coordinating solvents exist which may used in the preparation of CdSe dots. Organometallic precursors are selected for their stability, ease of preparation and clean decomposition products and low cracking temperatures. A particularly suitable organometallic precursor for use as a Cd source include alkyl cadmium compounds, such as $CdMe_2$. Suitable organometallic precursors for use as a Se source include, bis(trimethylsilyl)selenium (($TMS)_2Se$), (tri-n-octylphosphine)selenide (TOPSe) and trialkyl phosphine selenides, such as (tri-n-butylphosphine)selenide (TBPSe). Other suitable precursors may include both cadmium and selenium in the same molecule. Alkyl phosphines and alkyl phosphine oxide be used as a high boiling coordinating solvent; however, other coordinating solvents, such as pyridines, furans, and amines may also be suitable for the nanocrystallite production.

The preparation of monodisperse CdSe quantum dots has been described in detail in Murray et al. (J. Am. Chem. Soc., 115:8706 (1993)), which is hereby incorporated in its entirety by reference.

Next, the CdSe particles are overcoated by introducing a solution containing zinc and sulfur precursors in a coordinating solvent (e.g., TOP) into a suspension of CdSe nanocrystallites at the desired temperature. The temperature at which the dots are overcoated is related to the quality of the resultant composite particle. Overcoating the CdSe particles at relatively higher temperatures may cause the CdSe seed crystals to begin to grow via Ostwald ripening and deterioration of the size distribution of the particles leading to broader spectral line widths. Overcoating the particles at relatively low temperatures could lead to incomplete decomposition of the precursors or to reduced crystallinity of the ZnS shell. An ideal growth temperature may be determined for each CdSe core size to ensure that the size distribution of the cores remains constant and that shells with a high degree of crystallinity are formed. In preferred embodiments, CdSe crystallites are overcoated using diethyl zinc and hexamethyldisilathiane as the zinc and sulfur precursors. CdSe crystallites having a diameter in the range of about 23 Å-30 Å are overcoated at a temperature in the range of about 135-145° C., and preferably about 140° C. Similarly, nanocrystallites having a diameter of about 35 Å, 40 Å, 48 Å, and 55 Å, respectively, are overcoated at a temperature of about 155-165° C., and preferably about 160° C., 175-185° C. and preferably about 180° C., about 195-205° C., and preferably about 200° C., and about 215-225° C., and preferably about 220° C., respectively. The actual temperature ranges may vary, dependent upon the relative stability of the precursors and the crystallite core and overlayer composition. These temperature ranges may need to be modified 10-20° C., depending upon the relative stability of the precursors. For example, when the more stable trialkyl phosphine chalcogenides (like TOPSe) are used, higher temperatures are employed. The resulting (CdSe)ZnS composite particles are also passivated with TOPO/TOP on their outermost surface.

The ZnS precursor solution concentration and the rate of its addition to the CdSe particles is selected to promote heterogeneous growth of ZnS onto the CdSe nuclei instead of homogeneous nucleation to produce ZnS particles. Conditions favoring heterogeneous growth include dropwise addition, e.g., 1-2 drops/second, of the ZnS precursor solution to the CdSe solution and maintenance of the ZnS precursor solution at low concentrations. Low concentrations typically range from 0.0005-0.5 M. In some preferred embodiments, it may be desirable to include a final purification step in which the overcoated dots are subjected to size selective precipitation to further assure that mainly only (CdSe)ZnS composite particles are present in the final product.

In other embodiments, it may be desirable to modify the crystallite outer surface to permit formation of stable suspensions of the capped quantum dots. The outer surface of the nanocrystal includes an organic layer derived from the coordinating solvent used during the capping layer growth process. The crystallite surface may be modified by repeated exposure to an excess of a competing coordinating group. For example, a dispersion of the capped quantum dot may be treated a coordinating organic compound, such as pyridine, to produce crystallites which dispersed readily in pyridine, methanol, and aromatics but no longer dispersed in aliphatics. Such a surface exchange process may be carried out using a variety of compounds which are capable of coordinating or bonding to the outer surface of the capped quantum dot, such as by way of example, phosphines, thiols, amines and phosphates. In other embodiments, the capped quantum dots may be exposed to short chained polymers which exhibit an affinity for the capped surface on one and which terminate in a moiety having an affinity for the suspension or dispersion medium. Such affinity improves the stability of the suspension and discourages flocculation of the capped quantum dots.

The synthesis described above produces overcoated quantum dots with a range of core and shell sizes. Significantly, the method of the invention allows both the size distribution of the nanocrystallites and the thickness of the overcoating to be independently controlled. FIG. 1 shows the absorption spectra of CdSe dots with a particle size distribution of (a) 23 Å, (b) 42 Å, (c) 48 Å and (d) 55 Å in diameter before (dashed lines) and after (solid lines) overcoating with 1-2 monolayers of ZnS. By "monolayer" as that term is used herein, it is meant a shell of ZnS which measures 3.1 Å (the distance between consecutive planes along the [002] axis in the bulk wurtzite ZnS) along the major axis of the prolate shaped dots. The absorption spectra represents the wavelength and intensity of absorption of light which is absorbed by the quantum dot. FIG. 1 indicates a small shift in the absorption spectra to the red (lower energies) after overcoating due to the partial leakage of the exciton into the ZnS matrix. This red shift is more pronounced in smaller dots where the leakage of the exciton into the ZnS shell has a more dramatic effect on the confinement energies of the charge carriers.

Figure 2:
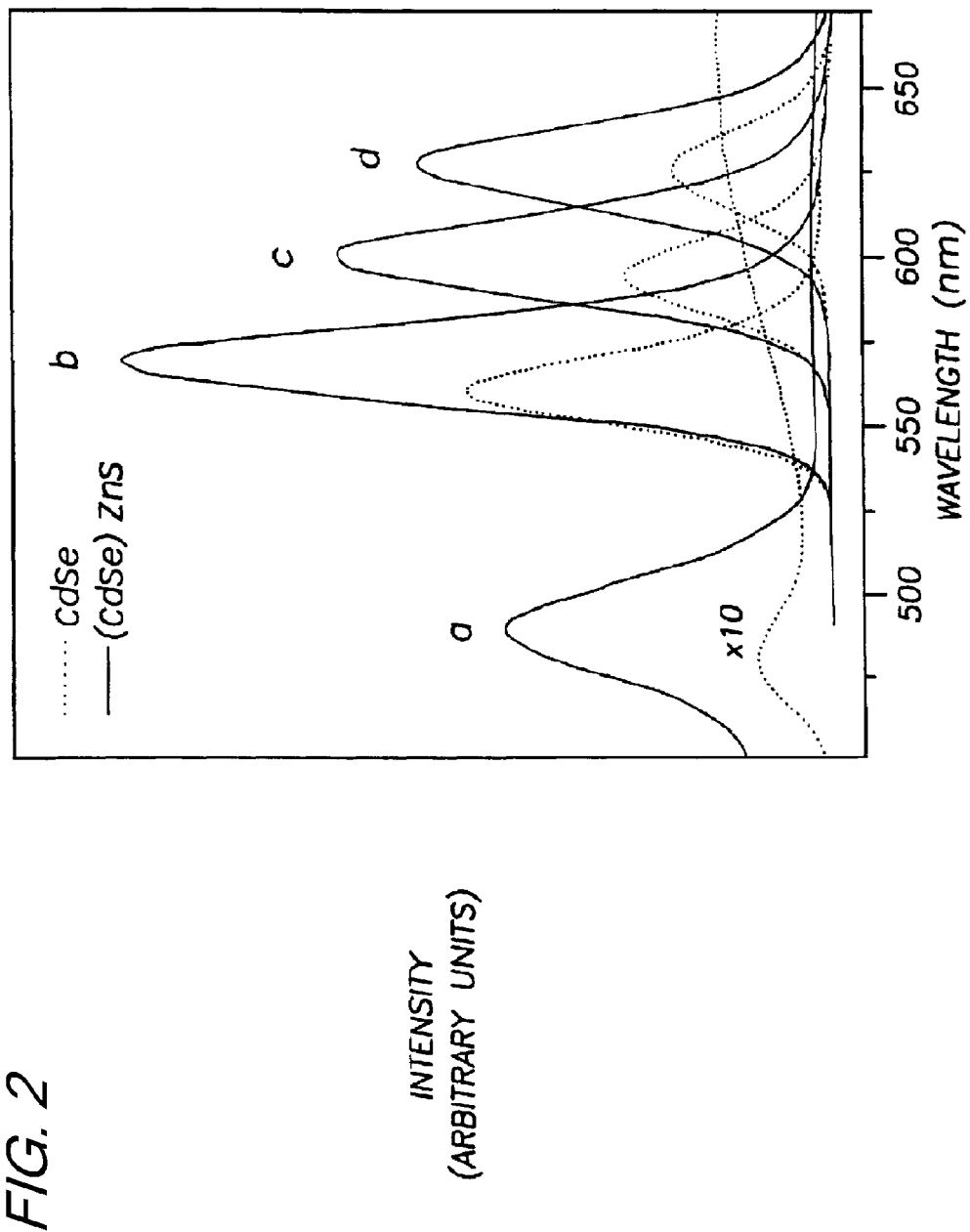
FIG. 2 shows the room temperature photoluminescence (PL) spectra of the samples of FIG. 1 before (dashed lines) and after (solid lines) overcoating with ZnS.

FIG. 2 shows the room temperature photoluminescence spectra (PL) of the samples shown in FIG. 1 before (dashed lines) and after (solid lines) overcoating with ZnS. The PL quantum yield increases from 5-15% for bare dots to values ranging from 30% to 50% for dots passivated with ZnS. The PL spectra are much more intense due to their higher quantum yield of (a) 40%, (b) 50%, (c) 35% and (d) 30%, respectively. The quantum yield reaches a maximum value with the addition of approximately 1.3 monolayers of ZnS. A decrease in quantum yields at higher ZnS coverages may be due to the formation of defects in the ZnS shell.

A color photograph demonstrates the wide spectral range of luminescence from the (CdSe)ZnS composite quantum dots of the present invention. See, for example, FIG. 3 of U.S. Pat. No. 6,207,229, which is incorporated by reference in its entirety. The photograph shows six different samples of ZnS overcoated CdSe dots dispersed in dilute hexane solutions and placed in identical quartz cuvettes. The samples were irradiated with 356 nm ultraviolet light from a uv lamp in order to observe luminescence from all solutions at once. As the size of the CdSe core increased, the color of the luminescence shows a continuous progression from the blue through the green, yellow, orange to red. Their PL peaks occur at (going from right to left in FIG. 3 of U.S. Pat. No. 6,207,229) (a) 470 nm, (b) 480 nm, (c) 520 nm, (d) 560 nm, (e) 594 nm and (f) 620 nm. In contrast, in the smallest sizes of bare TOPO-capped dots, the color of the PL is normally dominated by broad deep trap emissions and appears as faint white light.

Figure 3:
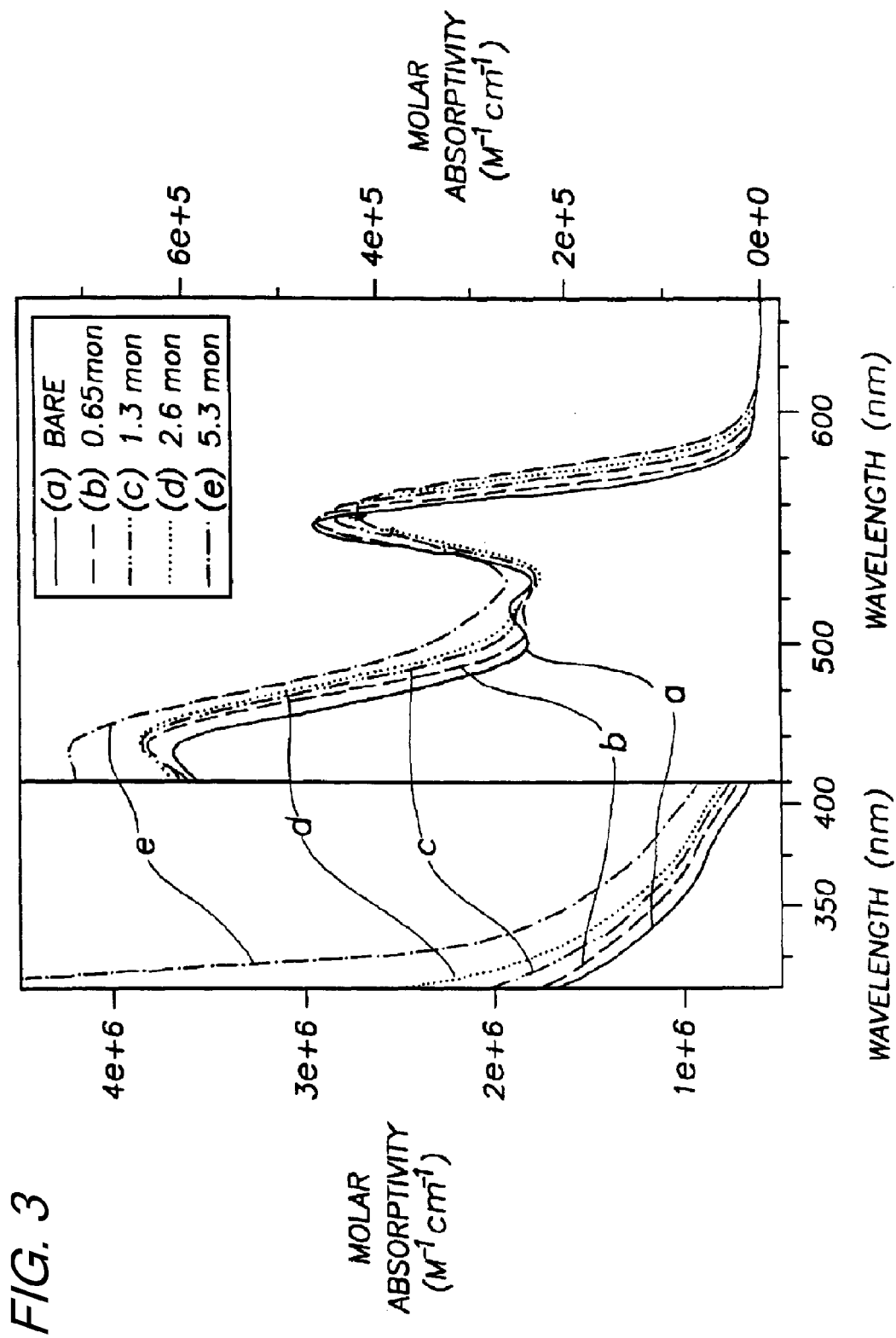
FIG. 3 shows the progression of the absorption spectra for (CdSe)ZnS quantum dots with ZnS coverages of approximately 0, 0.65, 1.3, 2.6 and 5.3 monolayers.

In order to demonstrate the effect of ZnS passivation on the optical and structural properties of CdSe dots, a large quantity of ~40 Å (±10%) diameter CdSe dots were overcoated with varying amounts of Zn and S precursors under identical temperatures and variable times. The result was a series of samples with similar CdSe cores, but with varying ZnS shell thicknesses. FIG. 3 shows the progression of the absorption spectrum for these samples with ZnS coverages of approximately 0 (bare TOPO capped CdSe), 0.65, 1.3, 2.6 and 5.3 monolayers. The right hand side of the figure shows the long wavelength region of the absorption spectra showing the lowest energy optical transitions. The spectra demonstrate an increased red-shift with the thicker ZnS overcoating as well as a broadening of the first peak in the spectra due to increased polydispersity of shell thicknesses. The left hand side of the spectra show the ultra-violet region of the spectra indicating an increased absorption at higher energies with increasing ZnS thickness due to direct absorption into the higher ZnS band gap ZnS shell.

Figure 4:
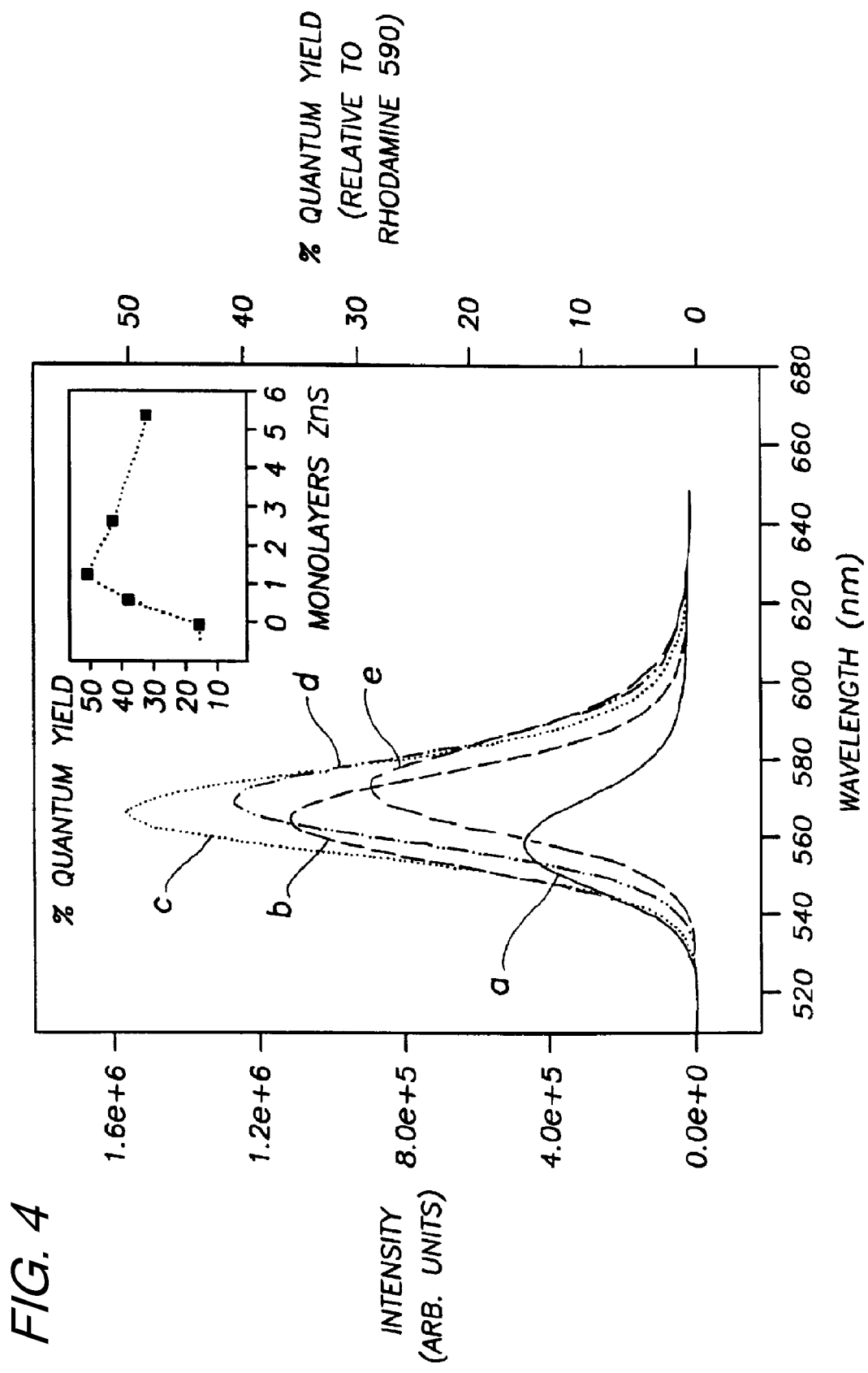
FIG. 4 shows the evolution of the PL for ~40 Å diameter (CdSe)ZnS dots of FIG. 3 with varying ZnS coverage.

The evolution of the PL for the same ~40 Å diameter CdSe dots with ZnS coverage is displayed in FIG. 4. As the coverage of ZnS on the CdSe surface increases one observes a dramatic increase in the fluorescence quantum yield followed by a steady decline after ~1.3 monolayers of ZnS. The spectra are red shifted (slightly more than the shift in the absorption spectra) and show an increased broadening at higher coverages. The inset to FIG. 4 charts the evolution of the quantum yield for these dots as a function of the ZnS shell thickness. For this particular sample, the quantum yield started at 15% for the bare TOPO capped CdSe dots and increased with the addition of ZnS approaching a maximum value of 50% at approximately ~1.3 monolayer coverage. At higher coverages, the quantum yield began to decrease steadily until it reached a value of about 30% at about 5 monolayers coverage.

Although the invention has been described with reference to the preparation and performance of CdSe(ZnS), it will be readily apparent that the method of preparation may be used to obtain monodisperse overcoated quantum dots with various combinations of nanocrystallite core and overcoating. The method of the invention permits the preparation of a variety of capped nanocrystals having a very narrow particle size distribution and exhibiting improvements in color purity and intensity of their photoluminescent emissions. It is contemplated that a variety of cadmium chalcogenides, for example, CdX, where X=S, Se, Te may be prepared and overcoated according to the method of the invention. It is further contemplated that the overcoating may be varied and may include, by way of example only, ZnS, ZnSe, CdS and mixtures thereof.

The invention is described with reference to the following examples, which are presented for the purpose of illustration and which are not intended to be limiting of the invention, the scope of which is set forth in the claims which follow this specification.

EXAMPLE 1

Preparation of CdSe. Trioctylphosphine oxide (TOPO, 90% pure) and trioctylphosphine (TOP, 95% pure) were obtained from Strem and Fluka, respectively. Dimethyl cadmium (CdMe$_2$) and diethyl zinc (ZnEt$_2$) were purchased from Alfa and Fluka, respectively, and both materials were filtered separately through a 0.2 μm filter in an inert atmosphere box. Trioctylphosphine selenide was prepare by dissolving 0.1 mols of Se shot in 100 ml of TOP thus producing a 1 M solution of TOPSe. Hexamethyl(disilathiane) (TMS$_2$S) was used as purchased from Aldrich. HPLC grade n-hexane, methanol, pyridine and n-butanol were purchased from EM Sciences.

The typical preparation of TOP/TOPO capped CdSe nanocrystallites follows. TOPO (30 g) was placed in a flask and dried under vacuum (~1 Torr) at 180° C. for 1 hour. The flask was then filled with nitrogen and heated to 350° C. In an inert atmosphere drybox the following injection solution was prepared: CdMe$_2$ (200 microliters, 2.78 mol), 1 M TOPSe solution (4.0 mL, 4.0 mmol), and TOP (16 mL). The injection solution was thoroughly mixed, loaded into a syringe, and removed from the drybox.

The heat was removed from the reaction flask and the reagent mixture was delivered into the vigorously stirring TOPO with a single continuous injection. This produces a deep yellow/orange solution with a sharp absorption feature at 470-500 nm and a sudden temperature decrease to ~240° C. Heating was restored to the reaction flask and the temperature was gradually raised to 260-280° C.

Aliquots of the reaction solution were removed at regular intervals (5-10 min) and absorption spectra taken to monitor the growth of the crystallites. The best samples were prepared over a period of a few hours steady growth by modulating the growth temperature in response to changes in the size distribution, as estimated from the sharpness of the features in the absorption spectra. The temperature was lowered 5-10° C. in response to an increase in the size distribution. Alternatively, the reaction can also be stopped at this point. When growth appears to stop, the temperature is raised 5-10° C. When the desired absorption characteristics were observed, the reaction flask was allowed to cool to ~60° C. and 20 mL of butanol were added to prevent solidification of the TOPO. Addition of a large excess of methanol causes the particles to flocculate. The flocculate was separated from the supernatant liquid by centrifugation; the resulting powder can be dispersed in a variety of organic solvents (alkanes, ethers, chloroform, tetrahydrofuran, toluene, etc.) to produce an optically clear solution.

Size-selective Precipitation. Nanocrystallites were dispersed in a solution of ~10% butanol in hexane. Methanol was then added dropwise to this stirring solution until opalescence persisted. Separation of supernatant and flocculate by centrifugation produced a precipitate enriched with the largest crystallites in the sample. This procedure was repeated until no further sharpening of the optical absorption spectrum was noted. Size-selective precipitation can be carried out in a variety of solvent/nonsolvent pairs, including pyridine/hexane and chloroform/methanol.

Surface Exchange. Crystallite surface derivatization can be modified by repeated exposure to an excess of a competing capping group. Heating to ~60° C. a mixture of ~50 mg of TOPO/TOP capped crystallites and 5-10 mL of pyridine gradually dispersed the crystallites in the solvent. Treatment of the dispersion with excess hexane resulted in the flocculation of the crystallites which are then isolated by centrifugation. The process of dispersion in pyridine and flocculation with hexane was repeated a number of times to produce crystallites which dispersed readily in pyridine, methanol, and aromatics but no longer dispersed in aliphatics.

EXAMPLE 2

Preparation of CdSe. A second route to the production of CdSe core replaces the phosphine chalcogenide precursors in Example 1 with (TMS)$_2$Se. The smallest (~12 Å) CdSe species are produced under milder conditions with injection and growth carried out at ~100° C. The product was further treated as described in Example 1.

EXAMPLE 3

Preparation of (CdSe)ZnS. Nearly monodisperse CdSe quantum dots ranging from 23 Å to 55 Å in diameter were synthesized and purified via size-selective precipitation as described in Example 1.

A flask containing 5 g of TOPO was heated to 190° C. under vacuum for several hours then cooled to 60° C. after which 0.5 mL trioctylphosphine (TOP) was added.

Roughly 0.1-0.4 μmols of CdSe dots dispersed in hexane were transferred into the reaction vessel via syringe and the solvent was pumped off.

Diethyl zinc (ZnEt$_2$) and hexamethyldisilathiane ((TMS)$_2$S) were used as the Zn and S precursors, respectively. The amounts of Zn and S precursors needed to grow a ZnS shell of desired thickness for each CdSe sample were determined as follows: First, the average radius of the CdSe dots was estimated from TEM or SAXS measurements. Next, the ratio of ZnS to CdSe necessary to form a shell of desired thickness was calculated based on the ratio of the shell volume to that of the core assuming a spherical core and shell and taking into account the bulk lattice parameters of CdSe and ZnS. For larger particles the ratio of Zn to Cd necessary to achieve the same thickness shell is less than for the smaller dots. The actual amount of ZnS that grows onto the CdSe cores was generally less than the amount added due to incomplete reaction of the precursors and to loss of some material on the walls of the flask during the addition.

Equimolar amounts of the precursors were dissolved in 2-4 mL TOP inside an inert atmosphere glove box. The precursor solution was loaded into a syringe and transferred to an addition funnel attached to the reaction flask. The reaction flask containing CdSe dots dispersed in TOPO and TOP was heated under an atmosphere of N$_2$. The temperature at which the precursors were added ranged from 140° C. for 23 Å diameter dots to 220° C. for 55 Å diameter dots. When the desired temperature was reached the Zn and S precursors were added dropwise to the vigorously stirring reaction mixture over a period of 5-10 minutes.

After the addition was complete the mixture was cooled to 90° C. and left stirring for several hours. Butanol (5 mL) was added to the mixture to prevent the TOPO from solidifying upon cooling to room temperature. The overcoated particles were stored in their growth solution to ensure that the surface of the dots remained passivated with TOPO. They were later recovered in powder form by precipitating with methanol and redispersing into a variety of solvents including hexane, chloroform, toluene, THF and pyridine.

In some cases, the as-grown CdSe crystallites were judged to be sufficiently monodisperse that no size-selective precipitation was performed. Once these CdSe particles had grown to the desired size, the temperature of the reaction flask was lowered and the Zn and S precursors were added dropwise to form the overcapping.

Optical Characterization. UV-Visible absorption spectra were acquired on an HP 8452 diode array spectrophotometer. Dilute solutions of dots in hexane were placed in 1 cm quartz cuvettes and their absorption and corresponding florescence were measured. The photoluminescence spectra were taken on a SPEX Fluorolog-2 spectrometer in front face collection mode. The room temperature quantum yields were determined by comparing the integrated emission of the dots in solution to the emission of a solution of rhodamine 590 or rhodamine 640 of identical optical density at the excitation wavelength.

What is claimed is:

1. A composition comprising a population of nanocrystals, wherein each nanocrystal of the population comprises a core including a first semiconductor material and an overcoating including a second semiconductor material deposited on the core, wherein the population exhibits a photoluminescence quantum yield of at least 30% and emits light in a spectral range of about 30 nm or less full width at half max (FWHM) when irradiated.

2. The composition of claim 1, wherein the population exhibits a photoluminescence quantum yield of at least 40%.

3. The composition of claim 1, wherein the population exhibits a photoluminescence quantum yield of about 50%.

4. The composition of claim 1, wherein the FWHM and quantum yield are determined at room temperature.

5. The composition of claim 1, wherein the cores of the population have diameters having no greater than 10% rms deviation.

6. The composition of claim 1, wherein the cores of the population have diameters having no greater than 5% rms deviation.

7. The composition of claim 1, wherein the spectral range has a peak in the range of about 470 nm to about 625 nm.

8. The composition of claim 1, wherein each of the cores has a diameter in the range of about 20 Angstroms to about 125 Angstroms.

9. The composition of claim 1, wherein the core comprises CdSe.

10. The composition of claim 9, wherein the overcoating comprises ZnS.

11. The composition of claim 1, wherein the overcoating has a uniform thickness over the entire nanocrystal.

12. A composition comprising a population of nanocrystals, wherein each nanocrystal of the population comprises a core including a first semiconductor material and an overcoating including a second semiconductor material deposited on the core, wherein the population exhibits photoluminescence having a quantum yield of at least 30% and the cores of the population have diameters having no greater than 5% rms deviation.

13. The composition of claim 12, wherein the population exhibits a photoluminescence quantum yield of at least 40%.

14. The composition of claim 12, wherein the population exhibits a photoluminescence quantum yield of about 50%.

15. The composition of claim 12, wherein the population of nanocrystals emits light in a spectral range of no greater than about 40 nm full width at half max (FWHM) when irradiated.

16. The composition of claim 12, wherein the population of nanocrystals emits light in a spectral range of no greater than about 30 nm full width at half max (FWHM) when irradiated.

17. The composition of claim 12, wherein the FWHM and quantum yield are determined at room temperature.

18. The composition of claim 12, wherein the FWHM and quantum yield are determined at room temperature.

19. The composition of claim 12, wherein the population of nanocrystals has a spectral range with a peak in the range of about 470 nm to about 621 nm when irradiated.

20. The composition of claim 12, wherein each of the cores has a diameter in the range of about 21 Angstroms to about 125 Angstroms.

21. The composition of claim 12, wherein the core comprises CdSe.

22. The composition of claim 12, wherein the overcoating comprises ZnS.

23. The composition of claim 12, wherein the overcoating has a uniform thickness over the entire core.

24. A composition comprising a population of nanocrystals, wherein the population comprises at least a first subpopulation of nanocrystals and a second subpopulation of nanocrystals,
   wherein each nanocrystal of the first and second subpopulation comprises a core including a first semiconductor material and an overcoating including a second semiconductor material deposited on the core, wherein the cores of the first population are monodisperse and the cores of the second population are monodisperse, wherein the cores of the first subpopulation differ in size from the cores of the second subpopulation;
   wherein the first and second subpopulations exhibit photoluminescence quantum yields of at least 30%; and
   wherein the first and second subpopulations each emit light in a spectral range of about 40 nm or less full width at half max (FWHM) when irradiated.

25. The composition of claim 24, wherein the first subpopulation and the second subpopulation each emits light in a spectral range of about 30 nm or less full width at half max (FWHM) when irradiated.

26. The composition of claim 25, wherein the FWHM is determined at room temperature.

27. The composition of claim 24, wherein the population exhibits a photoluminescence quantum yield of at least 40%.

28. The composition of claim 27, wherein the quantum yield is determined at room temperature.

29. The composition of claim 24, wherein the population exhibits a photoluminescence quantum yield of about 50%.

30. The composition of claim 29, wherein the quantum yield is determined at room temperature.

31. The composition of claim 24, wherein the cores of the first and second subpopulation comprise CdSe.

32. The composition of claim 31, wherein the overcoating of the first and second subpopulation comprises ZnS.

33. The composition of claim 24, wherein the cores of the first and/or second subpopulation have diameters having no greater than 10% rms deviation.

34. The composition of claim 24, wherein the cores of the first and/or second subpopulation have diameters having no greater than 5% rms deviation.

35. The composition of claim 24, wherein the FWHM is determined at room temperature.

36. The composition of claim 24, wherein the quantum yield is determined at room temperature.

37. The composition of claim 24, wherein the spectral ranges of the first and second subpopulations each have peaks in the range of about 470 nm to about 625 nm, wherein the peaks of the first and second subpopulations are distinct.

38. The composition of claim 24, wherein the cores of the first subpopulation have a diameter between 20 and 50 angstroms and the cores in the second subpopulation have a diameter between 50 and 125 angstroms.

* * * * *